(12) United States Patent
Schultz-Cherry et al.

(10) Patent No.: US 6,696,562 B1
(45) Date of Patent: Feb. 24, 2004

(54) AVIAN ASTROVIRUS

(75) Inventors: Stacey Schultz-Cherry, Oregon, WI (US); Laura Kelley, Fargo, ND (US); Matthew Koci, Middleton, WI (US); Bruce S. Seal, Athens, GA (US)

(73) Assignees: The United States of America as represented by the Secretary of Agriculture, Washington, DC (US); University of Georgia Research Foundation, Inc., Athens, GA (US)

( * ) Notice: Subject to any disclaimer, the term of this patent is extended or adjusted under 35 U.S.C. 154(b) by 144 days.

(21) Appl. No.: 09/900,920

(22) Filed: Jul. 10, 2001

Related U.S. Application Data

(60) Provisional application No. 60/217,312, filed on Jul. 10, 2000.

(51) Int. Cl.[7] .............................................. C07H 21/04
(52) U.S. Cl. ................ 536/23.72; 536/24.3; 536/24.33; 435/5; 435/91.2; 424/204.1
(58) Field of Search ............................. 536/23.72, 24.3, 536/24.33; 435/91.2, 5; 424/204.1

(56) References Cited

U.S. PATENT DOCUMENTS

| 5,556,746 A | 9/1996 | Herrmann et al. |
| 5,625,049 A | 4/1997 | Monroe et al. |

OTHER PUBLICATIONS

Heggen, C.L., et al., "Role of a Novel Virus in Pems and Associated Immune Functions", *ABMA*, No. 214, p. 49.

Koci, M.D., et al., "Direct Submission", Submitted (Mar. 28, 2000) USDA, ARS, Southeast Poultry Research Laboratory Athens, Georgia, Sequence update by submitter on Mar. 28, 2000.

Koci, M.D., et al., "Molecular Characterization of an Avian Astrovirus", *J. of Virology*, vol. 74, (13), pp. 6173–6177, Jul. 2000.

Reynolds, D., et al., "Astrovirus: A Cause of an Enteric Disease in Turkey Poults", *Avian Diseases*, vol. 30, (4), pp. 728–735, Apr. 1986.

Reynolds, D., et al., "Enteric Viral Infections of Turkey Poults: Incidence of Infection", *Avian Diseases*, vol. 31, (2), pp. 272–276, Aug. 1986.

Reynolds, D., et al., "A Survey of Enteric Viruses of Turkey Poults", *Avian Diseases*, vol. 31, (1), pp. 89–98, Jun. 4, 1986.

Saif, L., et al., "Enteric Viruses in Diarrheic Turkey Poults", *Avian Diseases*, vol. 29, (3), pp. 798–811, Feb. 11, 1985.

Saif, Y.M., et al., "A Small Round Virus Associated With Enteritis in Turkey Poults", *Avian Diseases*, vol. 34, pp. 762–764, 1990.

Hayhow, C., et al., "Development of an Antigen–Capture Enzyme–Linked Immunosorbent Assay for Detection of Enterovirus in Commercial Turkeys", *Avian Diseases*, vol. 37, pp. 375–379, 1993.

Thouvenelle, M., et al., "Astrovirus Infection in Hatchling Turkeys: Histologic, Morphometric, and Ultrastructural Findings", *Avian Diseases*, vol. 39, pp. 328–336, 1995.

Kurtz, J.B., et al., "Astroviruses: Human and Animal", *1987 Novel Diarrhoeaviruses*, Wiley, Chichester (Ciba Foundation Symposium 128), pp. 92–107.

*Primary Examiner*—Laurie Scheiner
(74) *Attorney, Agent, or Firm*—John D. Fado; Gail E. Poulos

(57) ABSTRACT

A unique turkey astrovirus has been isolated and sequenced. Primers and probes have been developed using the isolated nucleic acid sequence of the astrovirus and a reverse transcriptase PCR has been developed to detect the presence of avian astrovirus in commercial flocks. Furthermore, purified antigenic polypeptides have been synthesized from each of the open reading frames 1a,1b and 2 of the novel virus.

6 Claims, 23 Drawing Sheets

| | | | | | |
|---|---|---|---|---|---|
| TAstV | STPAYPKFQA | YDSEAEYLED | CGWQEYLDVV | SDP-ETINRR | PLWWCFL--- | 46 |
| HAstV-3 | STPAYPKMNY | FDTEEEYLEA | HGWAPYIREF | TRVFKGEKPE | VLWYLFLKKE | 50 |
| HAstV-1 | STPAYPKMNY | FDTEENYLEA | HGWAPYIREF | TRVFKGDKPE | VLWYLFLKKE | 50 |
| HAstV-2 | -------MNY | FDTEESYLEA | HGWAPYIREF | TRVFKGDKPE | VLWYLFLKKE | 43 |
| | | | | | | |
| TAstV | --KNEVLKRE | KIEDSDIRMI | LCTDPIFTRI | GAMFEQDQNN | RMKQQTEIRS | 94 |
| HAstV-3 | IIKEEKIK-- | ---NSDIRQI | VCADPIYTRI | GACLEAHQNA | LMKQHTGTSV | 95 |
| HAstV-1 | IIKEEKIR-- | ---NSDIRQI | VCADPIYTRI | GACLEAHQNA | LMKQHTDTSV | 95 |
| HAstV-2 | IIKEEKVK-- | ---NSDIRQI | VCADPIYTRI | GACLEAHQNA | LMKQHTDTSV | 88 |
| | | | | | | |
| TAstV | AQVGWTPFFG | GLDRRVRRLY | GDGDRYFVEM | DWTRYDGTIP | KSLFWRIRQI | 144 |
| HAstV-3 | GRCGWSPMEG | GFKKTMQRLV | NRGNRYFIEF | DWTRYDGTIP | PALFRHIKEI | 145 |
| HAstV-1 | GQCGWSPMEG | GFKKTMQRLV | NKGNKHFIEF | DWTRYDGTIP | PALFKHIKEI | 145 |
| HAstV-2 | GQCGWSPMEG | GFKKTMQRLV | NKGNKYFIEF | DWTRYDGTIP | PALFKHIKEI | 138 |
| | | | | | | |
| TAstV | RFFFLHDSHK | TPKMRRLYNW | YVKNLLEKII | LLPTGEVCQV | KKGNPSGQFS | 194 |
| HAstV-3 | RWNFINKDQR | E-KYRHVHEW | YVDNLINRHV | LLPSGEVTVQ | TRGNPSGQFS | 194 |
| HAstV-1 | RWNFINKDQR | E-KYRHVHEW | YVDNLINRHV | LLPSGEVTLQ | TRGNPSGQFS | 194 |
| HAstV-2 | RWNFINKDQR | E-KYRHVHDW | YVDNLINRHV | LLPSGEVTLQ | TRGNPSGQFS | 187 |
| | | | | | | |
| TAstV | TTVDNNMIAV | WLTTFEVSYL | FFKQRGRLPT | EKELQENCSM | IYGDDRILS | 244 |
| HAstV-3 | TTMDNNMVNF | WLQAFEFAYF | ----NG--P- | NKELWKTYDT | VYGDDRIST | 237 |
| HAstV-1 | TTMDNNMVNF | WLQAFEFAYF | ----NG--P- | DRDLWKTYDT | VYGDDRIST | 237 |
| HAstV-2 | TTMDNNMVNF | WLQAFEFAYF | ----NG--P- | DKDLWKTYDT | VYGDDRIST | 230 |
| | | | | | | |
| TAstV | IRKGFVEYEP | DTVIDMYKNI | FGMWVKRNNI | KIQDTPEGLS | FCGLTIVKSS | 294 |
| HAstV-3 | TPSVPDNYE- | ERVIAMYRDI | FGMWVKPGKV | ICRESIIGLS | FCGFTV-NSD | 285 |
| HAstV-1 | TPSVPDDYE- | ERVITMYRDI | FGMWVKPGKV | ICRDSIVGLS | FCGFTV-NEN | 285 |
| HAstV-2 | TPSVPDDYE- | ERVITMYRDI | FGMWVKPGKV | ICRNSIVGLS | FCGFTV-NEN | 278 |
| | | | | | | |
| TAstV | TGAYVGVPNV | NKILSTLENP | VRRLPDVESL | WGKL | SEQ ID NO: 50 | 328 |
| HAstV-3 | LEPVPTSP-- | EKLMASLLKP | YKVLPDLESL | HGKL | SEQ ID NO: 51 | 317 |
| HAstV-1 | LEPVPTSP-- | EKLMASLLKP | YKILPDLESL | HGKL | SEQ ID NO: 52 | 317 |
| HAstV-2 | LEPVPTSP-- | EKLMASLLKP | YKVLPDLESL | HGKL | SEQ ID NO: 53 | 310 |

FIG. 4

```
PV-1     VAILPTHASP GESIVIDGKE VEILDAKALE --DQAGTNLE ITIITLKRNE    48
HAstV-3  DIVTAAHVVG NNTFVNVCYE GLMYEAKV-- ---RYMPEKD IAFITCPGDL    45
HAstV-1  DIVTAAHVVG NNTFVNVCYE GLMYEAKV-- ---RYMPEKD IAFVTCPGDL    45
HAstV-2  DIVTAAHVVG NNTFVNVCYE GLMYEAKV-- ---RYMPEKD IAFITCPGDL    45
TAstV    YILTAEHVVQ GSDIATLKNG SVSVKSKVIK TIPIFESVDN VAVLKLPPEL    50

PV-1     KFRDIRPHIP TQITETNDGV LIVNTSKYPN MYVPVGAVTE QGYLNLGGRQ   109
HAstV-3  HPTARLKLSK NPDYSCVTVM AYVN--EDLV VSTAAAMVHG N-TLSYAVRT    93
HAstV-1  HPTARLKLSK NPDYSCVTVM AYVN--EDLV VSTAAAMVHG N-TLSYAVRT    93
HAstV-2  HPTARLKLSK NPDYSYVTVM AYVN--EDLV VSTAAAMVHG N-TLSYAVRT    93
TAstV    NSVKPIKLAK KVQSDYLTLT AYDPNFQHAV TFTGWCIIDG N-WLNNSFDT   100

PV-1     RAGQCGGVIT CT-GKVIGMHVG            SEQ ID NO: 54          128
HAstV-3  QDGMSGAFVC DKYGRVLAVH-Q TNTGYTGGA VIID  SEQ ID NO: 55    126
HAstV-1  QDGMSGAFVC DKYGRVLAVH-Q TNTGYTGGA VIID  SEQ ID NO: 56    126
HAstV-2  QDGMSGAFVC DKYGRVLAVH-Q TNTGYTGGA VIID  SEQ ID NO: 57    126
TAstV    KFGNSGAFYC DHDGRLVGIHLG TQGVL-QGI VIVD  SEQ ID NO: 58   134
```

FIG. 6

```
                    CA
                 A     A
                G       C
                U       A
                G       A
                 U : A
                 C : G
                 C : G
                 G : C
                 G : C
Slippery sequence G : C
                 G : C
GUC AAAGAAAC UAAUAG-A : U-ACCCCCGUACCAGAUUGGCUUAAAAUAUUUGCAUG
```

FIG. 7

```
   1 ccgaaagtgt tgtcggggcg atggcccagg cgggtcgcag tggcgatgct tttgcatccc
  61 ttgatcaacg gcgggagcgc caagaagaac aggcgcagtc cggccttgac aaggtgttct
 121 acttccaagg cgtggttgaa ctattcaacc gtatgaaaat cgcctatgga aggacaccgg
 181 cttggacggc cctcatgaag tgtaacgcca tatacttgaa agattttaaa acagcagttg
 241 gcgttgaggg tacccgctat gggctctttt tcgcagaaga agtgactaaa ccaacttggt
 301 cacccgacat tggagcaaac ttgataactt tgggcgaaaa ggcctgttta gacgcccaaa
 361 atgcaaaata tgaaagattg caagcctcac ttaaaacaac tagtggcctt gtgcatcaag
 421 tgatggaaaa aactagggaa gctaaagaga acctagagaa agccaataag atccaagagc
 481 aacttgacaa ggtcattgag agcaacaaag ctttacaccg taagatacag gagagaaacc
 541 gagaaaagat gcaggaatac atggtaaggt tgcataacac gcagaaagat cgtgatgatt
 601 gggttcagag atgctccagg ttagaacagg agaatgtcac attgcagaaa aggttgaagg
 661 agaaagagaa cgcgctggta tctgttgggt gggatctttt aggctggata gttatttcag
 721 tgcttgtatt cggcctgatt tcactcgcag acgcgcaaaa cttgactcca ccagccaaga
 781 ttgtgataac tccagggcaa gcagagttca tggacctagc taaattggaa aaaatccagg
 841 tcagaaagta ccgactggat agttgtgaat taccacctga gaaaggttgc gtgttgtaca
 901 aggattacct taccaccagg ccggtaagct tttggagtt gatggccaaa tgttcaaaac
 961 ctgactgggt ctcggagagc agttacaatg aaacaaccct aatggaagaa tgcatccaga
1021 tctttggtgc agagtggtgt gaagggaagc tcgttgatct tgtaccaaga aagtgtggcg
1081 agcaacatgt cttagttaac atcatagagc aaattgaaaa aaccagagaa gttgtgaccc
1141 ttatatatgg taaggtgatg tcatacaggc tagatatgtg gataacatct atttttagtt
1201 tagttttggc aggtaataag gaaaaattgt ttaaaatggc tcccttcatt tttgtagcat
1261 ggttttttaaa cataccagtg ttttaacttt gtgtggcagt caacattttt ccagttgttt
1321 ccctgccttt catttttgtc cagatttta tgccacagtt tgtttggta aatgcctttc
1381 ttctatggtt aacactcact ttaacagcat tttattggag tgagggccc aaaatactga
```

FIG. 12a

```
4861 tgttgaggag ttcgccgcca gagaaaacat acaacttcct gaggtcgggc ccgacttcta
4921 ttccagaata tggtgagagg aggaccgaaa gaagatggcg gcgatggccg acaaggtcgt
4981 tgtcaagaag acaactacaa ggcgcagggg caggagtaat tcccgctccc gtagcaggag
5041 taggagcagg agcagaacta aaaagacagt caaaattatt gagaaaaagc cagaaaaatc
5101 catcctaaag aaaattgatc aggctgaaag aagagatgca aaacagctta ggcggattcg
5161 taagaaagtg cagggaccgc cagtaaattc caggatgaca acagtagtca cacttggtca
5221 gataacaggc aataaagaca acaccctaga gcggaaacac aagtgctttc tgaatccgct
5281 gttgatgaag agtcaggaaa ctggtcaaac tgcaacaccc ttatctgtta gggcatccca
5341 atataatctg tggaagctat ccagactcca tgtcagactt atacccttg caggaaaagc
5401 gaatattttg gggtcagtgg tgttcttaga tcttgaacag gaggcaaaca cagcaggacc
5461 agaatcagta gataccatca aggcaagacc ccatgttgaa gttcccatag ggtcgaaaac
5521 cgtttggaaa gtgcaccata gaagcgctct aggacctaga caggggtggt ggaatgttga
5581 ccctggtgac agcccaactg attctcttgg gccagcactc aacatgtgga cctacctgca
5641 aactgtcaat gcactccaga gcgctggggg cactcaaacg ccttacacca gtgcactttt
5701 tcttgtggag gtcttggtca cttatgagtt ttcaaactat ggcccaaagc ctgcactgtc
5761 tcaaatggta tcagacagct ttccaccagc ctccggttct actgcaacct taaaaaacac
5821 cagtgatggg gctgtagcaa tacaactctc aggcgctatc gcccgaaaga tggaggaggt
5881 tgagcccaag ggtaggcgct caaatgcgca aacatcaggt gtcggtgaag tgttctgggc
5941 agtgtccact gaagtagtca atacagtagc agatgccata ccaggctggg gctggctcct
6001 gaaaggtggc tggtttgtcc ttaggaaaat ctttggggcc gcaaatgacc agaatggcac
6061 ttacttgata tactcttcag tggcagatgc acaaggtgac aacaggatat acacatcagt
6121 gaaacagaca cagttgacat caagcaggat caacctcgtc caactcaccc agcccaatgt
6181 gaaccaagca gcagtaggtg gcagtgttgg tgcggcaaac tccatctatt tgccactacc
6241 acaagcagat gaccaataca cacccctactt tgtctataat tttcaagggg aaagggtgtc
6301 aaccaccgag actggggtat tttgtctggc agccatacca gctgcgacta catctagtag
6361 gtataataat cagatcacca ctccatcaat tggctacagg aatgctagtg gtacaggaac
6421 atcattccta ctagatgctg catcatggtg gaatatattg gatgtaactc agactggagt
6481 gcttttttgga caaccaagat tgggtgttgg tgtcatgcag acaatgaaga ctctcaaaca
6541 gcatatcaag gattacacag agcctgcaat acagaaatat tatcctggaa caactaacct
6601 tgatgagcag ttgaagcaga gattgaacct ggcagagggt gacccggtca tctcaatggg
6661 ggacacaaac ggtaggaggg ctgcactctt ttataggact agtgatgaaa aatatatttt
6721 attttctca accacagaag atccaggggc acagtatcaa aatctgaaaa tgttgtactt
6781 ctggaactgg tcctattctg acacaaaaca gcaattttg gaccaccta gaacagtgca
6841 gtttgcaaat ttggatgaca gccagccagc cccctatgat agtgatgatg atgacctttc
6901 tgatgtaaca tcacttttg agcaggctga tttggggat gagacagact tcaaatttaa
6961 tatgtccatc caaacctcca aacatcttga ggaggagaaa aattactgga aaaaccagtg
7021 tgagaggatg atgatggaga aggccctttc gggcacctca cagcctcttg tccggtttga
7081 gaaagctgga cctagggcag accaatcttc tgccagtggt cattcttgaa tggccacact
7141 ttctctgcgg tggaaatgga aatcaccatt ccacctaaga tgattagccg atccaacgga
7201 aatcaccgt tgggtggtgc gcggtttacg catcgggaaa tcaacccggt gtattacccg
7261 cacttccggc tcaacagttt tttaaaactg atataaattt atgaaatttt tattagcatt
7321 ttaagaaaaa aaaaaaaaaa aaaaaaaaaa aaaaa
```

FIG. 12b

```
1441 tggagataag ttatgccctt gtgtatacca tcggctttgt tttatggtcc cttggactag
1501 ctgtggggt gacgctcaaa ttgacaatgg tacatcagat attaatgttt tgtgttgttg
1561 ccgcagctat ttgcggaacc aagtttgcat gcacaacaat aacagtgcaa cacccagatg
1621 gaacaaccgc aaaatacacc cgggttggta agctaaagaa taatgttgtg aaccagtgca
1681 aaaaggtagt cacgacattg cagacaagag gcgttatacc agcaacgcct gcgaaaacag
1741 catctattgt tattgttgag ggcaaaaatg gaacaggtgt tgggttcagg tttatgaatt
1801 atattcttac agcagaacac gtggttcagg gatcagatat agcaacactt aaaaatggca
1861 gtgttagtgt gaaatccaaa gtcatcaaaa cgatcccaat atttgagagt gttgacaatg
1921 ttgcagtgtt aaaattgcca cctgagctca atagcgtgaa gcctatcaaa ttagcaaaga
1981 aggttcaaag tgactatctg acactgacag cctatgatcc aaatttcaa catgccgcca
2041 cttttaccgg gtggtgtatt atagatggaa attggcttaa taactccttt gatacaaaat
2101 ttgggaatag tggtgcacct tattgtgatc atgatggtag gctagttggt atccacctag
2161 gcacacaggg tgttctttcc caaggcatag tcattgtaga cgcattgaaa aatacattcc
2221 agcttgcgga tcagtgtaga ccacagaatt ttgacatgga tgagttcctt gagaaagtta
2281 tagcaggaac aaaagtgtca catgcagcga tcctaaaaga actggaagaa cttagagaag
2341 aggtgcaatt tttaaagaaa aaatgtgtca cctatgatga ctactggcta tgccaaacca
2401 tctttgggca ggccaaaggg aagacgaaga aaacagtcag aggccgtaaa caccttgtta
2461 ccaaaagagc tcttgggaaa ggccacttca tgaagatgag gatgctcact gatgaagaat
2521 atcagaatat gattgaaaag ggcttctcag cagaggaaat aagggaggca gtcaacgcac
2581 tccgagaaca agcatggctt aattattgta ttgataatga tgttgatgac gaaggtgagg
2641 aagattggta tgatgacatg gtagagacag atagagttaa ccaggagatc gatgaggcca
2701 tagagcgggc catggaagat cgtggtgagt tctaccagaa gaaatcccgc cttacctttg
2761 ttgaacaggc catgatgcat ttgattcaag tgagcaagga gagaagccag actgctaaac
2821 tagaagttca aaaggagaat gaagcccaac tagtgaagat gtttgagcgg tgtgtcacag
2881 atgagaatac acctgagggt accacctcta tagcggcttt gtccacagaa gatgatgtta
2941 ggcttgttga agggaaagtc attgatttca ccaaagcaaa gaacatccca gttgacgggg
3001 aaattaggag agagatcatc cctggaacaa aatgtactga gatttccact ggacctgaaa
3061 ataagaagaa catattgaag aaaaaggata cacacatagc tgagggtaaa gttgaaacta
3121 agtcatcaca gcagccggtt gacgtcaagg atgataaacc cgtagccttg gaacaacgta
3181 agcctagagc ttgtaaatgg tgcggttcat cacagaaaca tgattaccgg gaatgtcggt
3241 ttcaacgtga aaaacgcttt tgtgtgtatt gtgcagctat gcactcaatg tttgagggcc
3301 atataagacc aatagagtgc actagttgca agaaaagttt ttcaggaatt gagaagttag
3361 aagatcatgt ggtcagtgga gagtgtcaaa aaaactaata gaggggcctg tgacaacaaa
3421 ggccctacc cccgtaccag attggcttaa aatatttgca tgggaagatg acatattacc
3481 acctgaaggt aaaactgcct taccagaaaa tgttactcta attggacata taccagttga
3541 taagttggtc tcgcgcacca agaaagtcca ggatccatta ttaggccttg taacaccatg
3601 gaaacaagat atgtatgatt caacaacatg gactgtaaag gcttacacca aaatgtttga
3661 gaaattccat taccacgacc cagttgactt tgtggaacag tatgctgagt ttgtgctgtt
3721 gtgtgacaat atggtgttga gagagcatga ctatatggca aatagcaaca tcacaccaat
3781 catgtcaaca gagaaaaatg tcaatagtac accagcatac ccaaaattcc aagcctatga
3841 cagcgaagcc gagtatttgg aagattgtgg gtggcaagag tacctggatt tgtgtctga
3901 tccagaaact ataaatcgta gaccctatg gtggtgcttc ctcaaaaatg aagttctcaa
3961 aagagagaaa attgaggaca gtgacattcg aatgatattg tgcaccgacc cgattttttac
4021 caggattggg gctatgtttg agcaggatca gaacaacaga atgaaacaac agactgaaat
4081 aaggtctgca caggtcggat ggaccccctt tttcggcggc ttggatcgca gggttcgcag
4141 gttgtatggt gatggagata ggtattttgt tgagatggac tggacacggt atgatgggac
4201 tataccaaaa tcactatttt ggagaattag gcaaatcagg ttcttcttcc tccatgattc
4261 tcataagact ccaaagatgc ggcgcttgta caactggtat gtgaaaaatc tgttggaaaa
4321 aattattta ttgccaactg gagaagtttg ccaggtcaag aaaggaaatc caagtggtca
4381 gttttcaaca actgtggata ataatatgat caatgtctgg ctaacaacat ttgaggtttc
4441 atacctattt ttcaaacagc gtggtagact gccaacagag aaagagctgc aagagaactg
4501 ctccatgata tgctacgggg atgacagact tctttccatc cgtaaagggt tgttgagta
4561 cgaacctgat acagtcattg atatgtacaa aacatcttt gaatgtggg tgaaaagaaa
4621 caacatcaaa atccaagata cacctgaagg gctctctttt tgtgggctta aatagtaaa
4681 atcaagtact ggtgcatatg ttggtgttcc caatgtgaac aaaatactgt caactttgga
4741 aaatccagta cgtaggctac cagatgttga gtctctttgg ggtaaattgg tttccctgcg
4801 catattgtgt gaaaatgctc ccagcaatgt taaacacttt cttgatgagc agattagcaa
```

FIG. 12c

/translation="MAQAGRSGDAFASLDQRRERQEEQAQSGLDKVFYFQGVVELFNR
MKIAYGRTPAWTALMKCNAIYLKDFKTAVGVEGTRYGLFFAEEVTKPTWSPDIGANLI
TLGEKACLDAQNAKYERLQASLKTTSGLVHQVMEKTREAKENLEKANKIQEQLDKVIE
SNKALHRKIQERNREKMQEYMVRLHNTQKDRDDWVQRCSRLEQENVTLQKRLKEKENA
LVSVGWDLLGWIVISVLVFGLISLADAQNLTPPAKIVITPGQAEFMDLAKLEKIQVRK
YRLDSCELPPEKGCVLYKDYLTTRPVSFLELMAKCSKPDWVSESSYNETTLMEECIQI
FGAEWCEGKLVDLVPRKCGEQHVLVNIIEQIEKTREVVTLIYGKVMSYRLDMWITSIF
SLVLAGNKEKLFKMAPFIFVAWFLNIPVFLTCVAVNIFPVVSLPFILFQIFMPQFVLV
NAFLLWLILTLTAFYWSEGPKILMEISYALVYTIGFVLWSLGLAVGVTLKLTMVHQIL
MFCVVAAAICGTKFACTTITVQHPDGTTAKYTRVGKLKNNVVNQCKKVVTTLQTRGVI
PATPAKTASIVIVEGKNGTGVGFRFMNYILTAEHVVQGSDIATLKNGSVSVKSKVIKT
IPIFESVDNVAVLKLPPELNSVKPIKLAKKVQSDYLTLTAYDPNFQHAATFTGWCIID
GNWLNNSFDTKFGNSGAPYCDHDGRLVGIHLGTQGVLSQGIVIVDALKNTFQLADQCR
PQNFDMDEFLEKVIAGTKVSHAAILKELEELREEVQFLKKKCVTYDDYWLCQTIFGQA
KGKTKKIVRGRKHLVTKRALGKGHFMKMRMLTDEEYQNMIEKGFSAEEIREAVNALRE
QAWLNYCIDNDVDDEGEEDWYDDMVETDRVNQEIDEAIERAMEDRGEFYQKKSRLTFV
EQAMMHLIQVSKERSQTAKLEVQKENEAQLVKMFERCVTDENTPEGTTSIAALSTEDD
VRLVEGKVIDFTKAKNIPVDGEIRREIIPGTKCTEISTGPENKKNILKKKDTHIAEGK
VETKSSQQPVDVKDDKFVALEQRKPRACKWCGSSQKHDYRECRFQREKRFCVYCAAMH
SMFEGHIRPIECTSCKKSFSGIEKLEDHVVSGECOKN".

FIG. 13

/translation="EVRRSCGQWRVSKKLIEGPVTTKAPTPVPDWLKIFAWEDDILPP
EGKTALPENVTLIGHIPVDKLVSRTKKVQDPLLGLVTPWKQDMYDSTTWTVKAYTKMF
EKFHYHDPVDFVEQYAEFVLLCDNMVLREHDYMANSNITHIMSTEKNVNSTPAYPKFQ
AYDSEAEYLEDCGWQEYLDVVSDPETINRRPLWWCFLKNEVLKREKIEDSDIRMILCT
DPIFTRIGAMFEQDQNNRMKQQTEIRSAQVGWTPFFGGLDRRVRRLYGDGDRYFVEMD
WTRYDGTIPKSLFWRIRQIRFFFLHDSHKTPKMRRLYNWYVKNLLEKIILLPTGEVCQ
VKKGNPSGQFSTTVDNNMINVWLTTFEVSYLFFKQRGRLPTEKELQENCSMICYGDDR
LLSIRKGFVEYEPDTVIDMYKNIFGMWVKRNNIKIQDTPEGLSFCGLTIVKSSTGAYV
GVPNVNKILSTLENPVRRLPDVESLWGKLVSLRILCENAPSNVKHFLDEQISNVEEFA
ARENIQLPEVGPDFYSRIW"

FIG. 14

/translation="MAAMADKVVVKKTTTRRRGRSNSRSRSRSRSRSRTKKTVKIIEK
KPEKSILKKIDQAERRDAKQLRRIRKKVQGPPVNSRMTTVVTLGQITGNKDNTLERKH
KCFLNPLLMKSQETGQTATPLSVRASQYNLWKLSRLHVRLIPLAGKANILGSVVFLDL
EQEANTAGPESVDTIKARPHVEVPIGSKTVWKVHPRSALGPRQGWWNVDFGDSPTDSL
GPALNMWTYLQTVNALQSAGGTQTPYTSALFLVEVLVTYEFSNYGPKPALSQMVSDSF
PPASGSTATLKNTSDGAVAIQLSGAIARKMEEVEPKGRRSNAQTSGVGEVFWAVSTEV
VNTVADAIPGWGWLLKGGWFVLRKIFGAANDQNGTYLIYSSVADAQGDNRIYTSVKQT
QLTSSRINLVQLTQPNVNQAAVGGSVGAANSIYLPLPQADDQYTPYFVYNFQGERVST
TETGVFCLAAIPAATTSSRYNNQITTPSIGYRNASGTGTSFLLDAASWWNILDVTQTG
VLFGQPRLGVGVMQTMKTLKQHIKDYTEPAIQKYYPGTTNLDEQLKQRLNLAEGDPVI
SMGDTNGRRAALFYRTSDEKYILFFSTTEDPGAQYQNLKMLYFWNWSYSDTKQQFLDH
LRTVQFANLDDSQPAPYDSDDDDLSDVTSLFEQADLGDETDFKFNMSIQTSKHLEEEK
NYWKNQCERMMMEKALSGTSQPLVRFEKAGPRADQSSASGHS"

FIG. 15

| | |
|---|---|
| aagcgctcta ggacctagac | SEQ ID NO 6 |
| ggaggtcttg gtcacttatg | SEQ ID NO 7 |
| gatagcgcct gagagttgta | SEQ ID NO 8 |
| attgccgcgc cacacttcac cgacacctga t | SEQ ID NO 9 |
| accagtgtga gaggatgatg | SEQ ID NO 10 |
| tattgccgcg cccggacaag agactgtgag gt | SEQ ID NO 11 |
| agaatgacca ctggcagaag | SEQ ID NO 12 |
| attgccgcgc ctcatcatcc tctcacactg g | SEQ ID NO 13 |
| tgttgaggag ttcgccgcca | SEQ ID NO 14 |
| tggcggcgaa ctcctcaaca | SEQ ID NO 15 |
| aataaggtct gcacaggtcg | SEQ IN NO 16 |
| cgacctgtgc agaccttatt | SEQ ID NO 17 |
| tccgctgttg atgaagagtc | SEQ ID NO 18 |
| gactcttcat caacagcgga | SEQ ID NO 19 |
| aactgttgag ccggaagtgc | SEQ ID NO 20 |
| cagagattga acctggcaga | SEQ ID NO 21 |
| ctgccaggtt caatctctgc | SEQ ID NO 22 |
| agcagcagta ggtggcagtg | SEQ ID NO 23 |
| cactgccacc tactgctgct | SEQ ID NO 24 |
| tggtgttgag agagcatgac | SEQ ID NO 25 |
| ggcctaataa tggatcctgg | SEQ ID NO 26 |
| ttgagcggtg tgtcacagat | SEQ ID NO 27 |

Fig. 16a

| | |
|---|---|
| atctgtgaca caccgctcaa | SEQ ID NO 28 |
| cactgacagc ctatgatcca | SEQ ID NO 29 |
| tggatcatag gctgtcagtg | SEQ ID NO 30 |
| agccgatggt atacacaagg | SEQ ID NO 31 |
| ccttgtgtat accatcggct | SEQ ID NO 32 |
| tgtggcgagc aacatgtctt | SEQ ID NO 33 |
| aagacatgtt gctcgccaca | SEQ ID NO 34 |
| ggcaagcaga gttcatggac | SEQ ID NO 35 |
| ggtccatgaa ctctgcttgc | SEQ ID NO 36 |
| agtggccttg tgcatcaagt | SEQ ID NO 37 |
| gatgcacaag gccactagtt | SEQ ID NO 38 |
| cctcatgaag tgtaacgcca | SEQ ID NO 39 |
| cctgttcttc ttggcgctcc | SEQ ID NO 40 |
| ggagcgccaa gaagaacagg | SEQ ID NO 41 |
| aatatgatca atgtctggct | SEQ ID NO 42 |
| ccmctvtggt ggtgcttcct | SEQ ID NO 43 |
| ggcccgacyt caggaagt | SEQ ID NO 44 |
| tcgttaatta accgaaagtg ttgtc | SEQ ID NO 45 |
| gaaagtgttg tcggggcgat | SEQ ID NO 46 |
| cggtgaattc ccgaaagtgt tgtcg | SEQ ID NO 47 |
| agcctccggt tctactgcaa | SEQ ID NO 48 |
| ttgcagtaga accggaggct | SEQ ID NO 49 |

Fig. 16b

AVIAN ASTROVIRUS

CROSS REFERENCE TO PROVISIONAL APPLICATION

This application claims benefit to copending provisional application Ser. No. 60/217,312, filed Jul. 10, 2000.

BACKGROUND OF THE INVENTION

1. Field of the Invention

This invention relates to biological methods and products useful in agriculture. More specifically, the present invention is directed to a novel turkey astrovirus, nucleic acid encoding the novel turkey astrovirus, primers sequences to the novel turkey astrovirus, methods for detecting avian astroviruses, and vaccines to avian astroviruses.

2. Description of the Related Art

Astroviruses are small nonenveloped, positive sense RNA viruses, which are distinct among the other closely related small round, positive stranded RNA viruses such as calciviruses and picornaviruses (Carter, Arch. Virol. Suppl., Volume 9, 429–439, 1994; Monroe et al., J. Virol., Volume 67, 3611–3614, 1993; Willcocks et al., J. Gen. Virol., Volume 75, 1785–1788, 1994). Astroviruses cause enteric disease in the young of several species including mammals and poultry (Aroonprasert et al., Vet. Microbiol., Volume 19, 113–125, 1989; Bridger et al., Infect. Immun., Volume 43, 133–138, 1984; Geyer et al., J. S. Afr. Vet. Assoc., Volume 65, 164–166, 1994; Gorbalenya et al., FEBS Lett., Volume 243, 103–114, 1989; Harbour et al., Vet. Rec., Volume 120, 555–557, 1987; Herring et al., J. Gen. Virol., Volume 53, 47–55, 1981; Hoshino et al., Arch. Virol., Volume 70, 373–376, 1981; Kjedlsberg et al., Arch. Virol., Volume 84, 135–140, 1985; Marshall et al., Aust. Vet. J., Volume 61, 33–38, 1984; Matsui et al, In: Fields Virology, third edition, Fields et al. (Eds.), Lippincott-Raven, Publishers, Philadelphia, Volume 1, 811–824, 1996; McNulty et al., Vet. Rec., Volume 106, 561, 1980; Reynolds et al., Avian Dis., Volume 30, 728–735, 1986; Shimizu et al., J. Clin. Microbiol., Volume 28, 201–206, 1990; Snodgrass et al., Arch. Virol., Volume 55, 287–291, 1977; Tzipor et al., Vet. Rec., Volume 108, 286, 1981; Williams, Arch. Virol., Volume 66, 215–226, 1980; Woode et al., J. Med. Microbiol., Volume 11, 441–452, 1978) as well as fatal hepatitis in ducklings (Gough et al., Vet. Rec., Volume 114, 279, 1984).

Astrovirus disease in humans is one of the major causes of diarrhea in infancy and childhood. Greater-than 70% of children in the United States develop astrovirus antibodies before the age of 5 (Cook et al, J. Med. Microbiol., Volume 42, 1–2, 1995). Eight human astrovirus serotypes have been identified, and these are the only viruses within the family wherein the genome has been completely sequenced (Matsui et al., 1996, supra; Monroe et al, U.S. Pat. No. 5,625,049, Apr. 29, 1997).

Astroviruses cause outbreaks of enteric disease in turkey poults. Astrovirus was first reported as a cause of gastroenteritis and mortality of turkeys 6 to 11 days of age in 1980 by McNulty et al (1980, supra). Since then there have been sporadic reports of astrovirus outbreaks in turkeys mostly related to enteritis and growth depression ( Reynolds et al., 1986, supra). Little is understood about astrovirus infection in turkeys, and detection has been dependent on EM and fluorescent antibody tests. However, this may be a function of the tools currently available for the diagnosis of astrovirus infections.

The human astrovirus has been described as approximately 6800 nucleotides (nt), and is organized into three open reading frames (ORF); 1a, 1b, and 2. From the 5' end of the genome ORF 1a codes from the non-structural proteins identified as a serine protease, transmembrane helices, and a nuclear localization signal respectively (Cubitt, Arch. Virol. Suppl., Volume 12, 225–235, 1996). Next ORF 1b codes for the RNA dependent RNA polymerase (RDRP). ORFs 1a and 1b overlap by approximately 70 nt. ORF 1b is brought into frame by a retrovirus-like frameshift sequence that produces a stem loop (Marczinke et al., J. Virol., Volume 68, 5588–5595, 1994). At the 3' end of the genome is ORF 2 which codes the capsid protein and is followed by an untranslated region and polyadenylated tail. ORF 2 is transcribed into a subgenomic message of approximately 2500 nt (Cubit, 1996, supra).

Detection of astrovirus in most species is limited to fluorescent antibody detection, and electron microscopy (EM). Both of these methods are time intensive and vulnerable to misdiagnosis. Fluorescent antibody tests may fail to recognize astrovirus antigens if the sample is infected with a different serotype (Matsui et al., 1996, supra). EM can also fail to detect the characteristic star-like surface projections, if the. sample is not processed correctly ( Caul et al., J. Med. Virol., Volume 9(4), 257–265, 1982). Furthermore, detection by cell culture is currently limited to bovine, feline, porcine, and human astroviruses (Harbour et al., 1987, supra; Lee et al., J. Gen., Virol., Volume 57 (2), 421–424, 1981; Shimuzu et al., 1990, supra; Woode et al., J. Clin. Microbiol., Volume 19 (5), 623–630, 1984).

While various astroviruses are known to cause enteric disease in several animal species including humans, there remains a need in the art for methods for detecting astrovirus in avians, especially poultry, which overcome some of the limitations of related art detection methods. The present invention described below is a novel turkey astrovirus, a novel nucleic acid encoding the turkey astrovirus, primers and probes for in-situ hybridization to avian astrovirus, methods for detecting the avian astrovirus using primers designed from the sequence of the novel turkey astrovirus, and vaccines to avian astroviruses. The present invention further describes antigenic polypeptides synthesized from the open reading frames 1a, 1b, and 2 of the novel turkey astrovirus nucleic acid.

SUMMARY OF THE INVENTION

It is, therefore, an object of the present invention to provide a novel turkey astrovirus for antigen production, vaccine production, antibody production, diagnostic primer or probe production, etc.

It is another object of the present invention to provide a turkey astrovirus nucleic acid sequence for production of antigenic polypeptides, vaccines, antibodies, primers, and probes for in-situ hybridization.

Another object of the present invention is to provide methods for detecting astrovirus in avians, especially poultry, more specifically turkeys, using antibodies, primers, or probes produced from a novel turkey astrovirus nucleic acid sequence.

A further object of the present invention is to provide a vaccine using a turkey astrovirus and/or a turkey astrovirus nucleic acid sequence.

Further objects and advantages of the present invention will become apparent from following description.

BRIEF DESCRIPTION OF THE DRAWINGS

In FIG. 2A, the overlapping clones generated by 5' Race, represented by black arrows, have amino acid similarities to the section of the corresponding astrovirus genome. Numbers above the arrows designate the clone used to generate that portion of the sequence data. Each cycle of 5' Race generated several clones of overlapping sequence identity. Clones listed are representative of 3 to 4 individual constructs. FIG. 2B shows the location of primers used. ORF 1b codes for the viral polymerase and ORF 2 codes for the capsid protein. Primers MKPOL11 and MCPOL10 produce approximately an 802 bp fragment from the 3' end of ORF 1b. Primers MKCAP19 and MKCAP8 produce an 849 bp fragment for the 3' end of ORF 2.

FIG. 4 shows four protein sequences with identification of an RNA dependent RNA polymerase active site and comparison to human astrovirus type-1 (HastV-1; SEQ ID NO 52), type-2 (HastV-2; SEQ ID NO 53), and type-3 (HastV-3; SEQ ID NO 51). The conserved active site motif is boxed in bold letters. Amino acid similarities to TastV (SEQ ID NO 50) are italicized, and underlined amino acids indicate conserved positions described by Poch et al. (Embo J., Volume 8, 3867–3874, 1989).

FIG. 6 shows four protein sequences with the comparison of the cysteine protease of human poliovirus (PV-1; SEQ ID NO 54), the serine protease sequence of human astroviruses types 1 (HastV-1; SEQ ID NO 56), 2 (HastV-2; SEQ ID NO 57), and 3 (HastV-3; SEQ ID NO 55), and the putative serine protease of turkey astrovirus (TastV, SEQ ID NO 58). The suspected catalytic triad for each virus is represented in bold and underlined (Willcocks et al., 1994, supra). Amino acid matches between TAstV and the HAstV isolates are shown in italics. (^) Position implicated in substrate binding, TAstV has glycine substituted for alanine. (#) Additional substrate binding site, histadines are present all sequences compared.

FIG. 7 shows predicted secondary structure of the frameshift between ORF 1a and 1b (SEQ ID NO 59). The heptanucleotide "slippery" sequence, documented in the astroviruses sequenced thus far, was identified in the turkey astrovirus of the present invention and highlighted in the gray box.

FIGS. 12A–12C represent a DNA sequence (SEQ ID NO 1) for the novel turkey astrovirus.

FIG. 13 is an amino acid sequence (SEQ ID NO 60) for the putative serine protease which is a translation of the ORF 1a of the turkey astrovirus.

FIG. 14 is an amino acid sequence translation (SEQ ID NO 61) from an alternate site of translation initiation of ORF1B of the turkey astrovirus.

FIG. 15 is an amino acid sequence translation (SEQ ID NO 62) from the ribosomal frameshift slippery site.

FIGS. 16A and 16B shows/DNA sequences for other useful primers of the present invention (SEQ ID NOs 6–49).

DETAILED DESCRIPTION OF THE INVENTION

Figure 1:
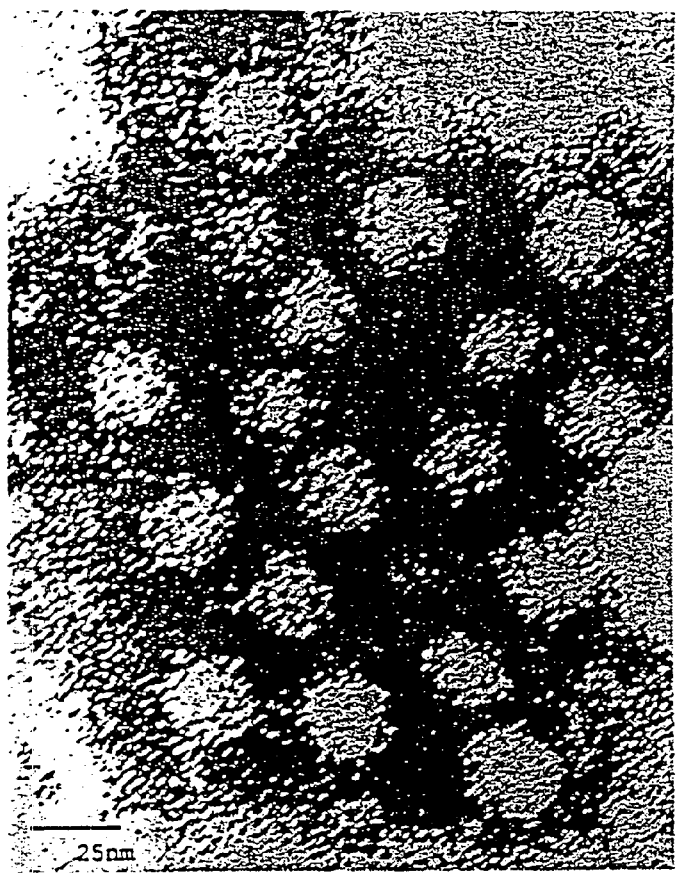
FIG. 1 is an electron micrograph of 25 nm viral particles.

The novel turkey astrovirus of the present invention was isolated from turkeys affected by an emerging disease, which is characterized by enteritis, high mortality, growth depression, lymphoid atrophy, and immunosuppression; clinical signs similar to Poult Enteritis Mortality syndrome (PEMS). When the virus of the present invention is given to naive turkeys, it induces clinical signs similar to PEMS. It is because of this lymphoid atrophy and immunosuppression that the thymus was examined as the source of disease agents, which led to the isolations and subsequent molecular characterization of the astrovirus of the present invention. This virus can be readily detected in the intestines, thymus, and bursa of infected poults, using both electron microscopy and Reverse Transcriptase-PCR (RT-PCR). The identity of the virus of the present invention is based on sequence similarities to astrovirus as well as the identification of several distinctive astrovirus properties. These comparisons showed TAstV to be about 7,325 nt (excluding the poly(A) tail) in length. The sequence is made up of Open Reading Frame (ORF) 1a, ORF 1b and ORF 2. Each ORF codes for proteins with limited amino acid similarity to HAstV. The predicted proteins within this viral genome are designated as a serine protease (ORF 1a), an RNA-dependendent RNA polymerase (RDRP) (ORF 1b), and a viral capsid protein (ORF 2). Also detected was a retroviruslike frameshift signal with potential secondary structure in the genome.

Each of these elements is consistent with other sequenced astroviruses and establish this newly described virus as being a TAstV. An embryonated turkey egg system was developed to culture the virus to high titers. When naive poults are given the purified virus of the present invention, they exhibit enteritis, high mortality, growth depression, lymphoid atrophy, and immunosuppression.

The present invention provides an isolated nucleic acid encoding turkey astrovirus as set forth in SEQ ID NO. 1 and depicted in FIG. 12. The invention also provides a nucleic acid capable of selectively hybridizing DNA, RNA, and cDNA sequences which can be derived from SEQ ID NO 1. While SEQ ID NO 1 is a DNA sequence, the invention also provides the corresponding RNA sequence. In order to isolate the TAstV virus with high titers, thymus from turkey poults exhibiting diarrhea is homogenized in phosphate-buffered saline (PBS). The homogenized tissue is then clarified by low speed centrifugation and filtered to remove bacteria. A novel embryonated turkey egg system was developed to culture the virus to high titers. The filtered composition is then inoculated into the yolk sac of approximately 20-day-old specific pathogen-free (SPF) turkey embryos. The eggs are incubated for about 5 days at about 37° C. Pools of intestine, intestinal fluids, and bursas are harvested from the inoculated embryos, homogenized, clarified, and filtered as above and again the resulting filtered composition is inoculated into the yolk sac of SPF turkey embryos. This procedure is repeated for about three more times. After final passage, embryo intestines, fluid, and bursa are again harvested, homogenized, clarified, and filtered as above. This time the filtrate is centrifuged at about 20,000 to about 30,000 ×g for about three to eight hours in a fixed angle rotor. The pellet containing virus is resuspended in TRIS-0.25 M EDTA (TE) buffer, at about pH 7.0. This suspension is then overlaid on about a 27%/37% CsCl gradient and ultra-centrifuged from about 20,000 rpm to about 25,000 rpm for about 12–18 hours. The faint band above the gradient layer is removed with a syringe, diluted with TE buffer, and centrifuged at about 20,000 to about 30,000 ×g for about 3 hours in a fixed angle rotor. The resulting pellet is then resuspended in a diluent such as for example PBS, TBS, water or TE, to form a purified TAstV-containing composition. Alternatively, the virus can be purified by one of ordinary skill in the art using size exclusion chromatography.

For purposes of the present invention, the term "isolated" is defined as separated from other nucleic acids found in naturally occurring organisms. The recitation "capable of selectively hybridizing" is defined as a sequence which does not hybridize with other nucleic acids to prevent adequate positive hybridization with nucleic acids from avian astroviruses.

Currently there are no reagents available to diagnose or control astrovirus infection in avians, especially poultry. For purposes of the present invention avian is defined as any bird which may be infected with an astrovirus and especially including, for example, turkeys, chickens, geese, ducks, ostrich, emu, pheasant, etc. The presence of an avian astrovirus such as TAst-V can be determined by detecting the presence of a nucleic acid specific for avian astroviruses, especially turkey astrovirus. The present invention provides a method of detecting the presence of avian astrovirus in a sample comprising detecting the presence of the nucleic acid encoding an avian astrovirus. The nucleic acid specific for avian astrovirus can be detected utilizing nucleic acid amplification techniques such as those disclosed in U.S. Pat. 5,625,049 (Monroe et al., Apr. 29, 1997; herein incorporated by reference).

An aspect of the present invention is the development of a Reverse Transcriptase-PCR method for detecting astrovirus infection in poultry. Primers were designed from both highly conserved and potential variable regions of the first completely sequenced TAstV genome (SEQ ID NO 1; GENBANK accession number:AF206663). The present invention includes RT-PCR methods directed to both the ORF 1b and 2 regions allowing for detection of TAstV isolates closely related to the virus of the present invention using capsid gene specific primers from ORF 2. The methods also allow detection of astrovirus infection in commercial poultry flocks for other serotypes which may arise using polymerase specific primers from ORF 1b.

Given the knowledge of the nucleotide sequence of TAst-V, synthetic oligonucleotides can be prepared which are complementary to the nucleic acid of interest. Each nucleotide sequence is complementary to one of two strands. It is well within the ordinary skill in the art to use any portion of the novel turkey astrovirus genome to design specific primers or probes for diagnostic tests using any computer program designed to analyze nucleotide sequences such as for example, Vector NTO, OLIGO, or Jellyfish (BioWire). Examples of useful primers of the present invention include MKCAP8: TCATCATCCTCTCACACTGG (SEQ ID NO 2), MKCAP19: AGCAGCAGTAGGTGGCAGTG (SEQ ID NO 3), MKPOL10: TGGCGGCGAACTCCTCAACA (SEQ ID NO 4), and MKPOL11: AATAAGGTCTGCACAG-GTCG (SEQ ID NO 5). Primers MKCap8 and 19 produce an 849 base pair (bp) amplicon from within the viral capsid gene. Primers MKPOL10 and 11 produce an 802 bp fragment overlapping the viral polymerase ORF. Other useful primers are included in FIG. 16 (SEQ ID NOs. 6–49)

The polymerase chain reaction (PCR) and reverse transcriptase PCR are techniques that amplify nucleic acid sequences with remarkable efficiency. In the PCR step of the present method, repeated cycles of denaturation, primer annealing and extension carried out with polymerase, e.g., a heat stable enzyme Taq polymerase, leads to exponential increases in the concentration of desired nucleic acid sequences. The method of the present invention includes the following steps:

(A) isolation of total RNA from a sample to be tested;
(B) synthesis of first strand DNA from the isolated RNA using a reverse primer selected from MKCAP8, MKCAP19, MKPOL10, and MKPOL11;
(C) amplification of first strand DNA using the primer selected for use in step (B);
(D) Detection of PCR products of step C.

TAstV can be detected by RT-PCR using primers designed from the TAstV, such as for example, MKCAP 8, MKCAP19, MKPOL10, and MKPOL11. The method includes isolating total RNA from a sample to be tested. Samples include for example, intestines, bursa, thymus, feces, spleen, kidney, and pancreas. Samples can also include litter from infected houses and biological vectors such as, for example, darkling beetles. Total RNA for purposes of the present invention means all RNA found in the test sample which is capable of being extracted using any method established in the prior art for extracting RNA. For purposes of the present invention, total RNA can be obtained by methods and/or kits well established in the art such as, for example, TRIzol® Total RNA Isolation Reagent (Life Technologies™, Rockville, Md.), Rneasy (Qiagen), Oligotex RNA kit, Qiamp viral RNA kit, etc. The isolated RNA is then used as a template to generate first strand cDNA using primers, such as for example, MKCAP 8, MKCAP19, MKPOL10, and MKPOL11. For purposes of the present invention, first strand DNA is defined as initial DNA transcript produced from isolated viral DNA. Extracted total RNA is incubated with a primer such as, for example, MKCAP 8, MKCAP19, MKPOL10, and MKPOL11, Reverse transcriptase, such as for example, MMLV, Superscript, SuperScript II, etc., and dNTPs at about 37–60° C. For purposes of the present invention, the amounts of each of the reagents should be effective for producing first strand cDNA in a quantity useful for amplification of the first strand cDNA.

The first strand CDNA produced above is amplified using the primer used to produce the cDNA. For purposes of the present invention, the amounts of each of the amplification reagents should be effective for amplifiying the first strand cDNA in a quantity useful for detection. First strand cDNA produced in the second step is incubated with primer, dNTPs, approximately 1.5 mM $MgCl_2$, and Taq DNA polymerase. The amplified product is then electrophoresed in TAE buffer and visualized by staining and ultraviolet irradiation. Agarose or polyacrylamide are examples of gels useful for electrophoresis. Any intercalating agents such as, for example, ethidium bromide, Sybr green, acridine orange, etc., is useful for detection using ultraviolet light. For purposes of the present invention, any technique known in the art can be used for detecting the amplified product. Each test includes a positive TAstV control and a negative control using uninfected tissues.

The turkey astrovirus of the present invention can be used to provide purified antigenic polypeptide fragments encoded by the nucleic acids of the present invention. As used herein, "purified" means the antigen is at least sufficiently free of contaminants or cell components with which the antigen normally occurs to distinguish the antigen from the contaminants or components. Purified turkey astrovirus antigen and antigenic fragments are also referred to herein as the antigen or the turkey astrovirus antigen or the TastV antigen. It is contemplated that the antigenic fragments can be encoded from any portion of the nucleic acid encoding the turkey astrovirus of the present invention as set forth in the sequence listing as SEQ ID NO. 1, but especially for fragments encoded by the open reading frames 1a, 1b, and 2. Specifically, one example provides a polypeptide antigen encoded by open reading frame 2, the capsid protein consisting of amino acids encoded by nucleotides 4995 through 7129, contained in the nucleotide sequence set forth in the sequence listing as SEQ ID NO 1. Other examples are polypeptide antigens encoded by open reading frame la, the serine protease consisting of amino acids encoded by nucleotides 21/153 through 3398; and open reading frame 1b, the polymerase consisting of amino acids encoded by nucleotides 3353 through 4936.

An antigenic fragment can be isolated from the whole antigen by chemical or mechanical disruption. The purified fragments thus obtained can be tested to determine their antigenicity and specificity by the methods taught herein. Antigenic fragments can also be synthesized directly. An immunoreactive fragment is generally an amino acid sequence of at least about five consecutive amino acids derived from the antigen amino acid sequence.

The polypeptide fragments of the present invention can also be recombinant proteins obtained by cloning nucleic acids encoding the polypeptide in an expression system capable of producing the antigenic polypeptide or fragments thereof.

Once the amino acid sequence of the antigen is provided, it is also possible to synthesize, using standard peptide synthesis techniques, peptide fragments chosen to be homologous to immunoreactive regions of the antigen and to modify these fragments by inclusion, deletion, or modification of particular amino acid residues in the derived sequences. Thus, synthesis or purification of an extremely large number of peptides derived from the antigen is possible.

The amino acid sequences of the present polypeptides can contain an immunoreactive portion of avian astrovirus antigen attached to sequences designed to provide for some additional property, such as solubility. The amino acid sequences of the avian astrovirus antigen can include sequences in which one or more amino acids have been substituted with another amino acid to provide for some additional property, such as to remove/add amino acids capable of disulfide bonding, to increase its bioactivity, alter enzymatic activity, or alter interactions with gastric acidity. In any case, the peptide must possess a bioactive property, such as immunoreactivity, immunogenicity, etc.

The purified polypeptide fragments thus obtained can be tested to determine their immunogenicity and specificity. Briefly, various concentrations of a putative immunogenically specific fragment are prepared and administered to an animal and the immunological response (e.g. production of antibodies or cell mediated immunity) of an animal to each concentration is determined. The amounts of antigen administered depend on the subject, the condition of the subject, the size of the subject, etc. Thereafter, an animal so inoculated with the antigen can be exposed to the virus to test the potential vaccine effect of the specific immunogenic fragment. The specificity of the putative immunogenic fragment can be ascertained by testing sera or other fluids or lymphocytes from the inoculated animal for cross reactivity with other closely related astroviruses.

A vector comprising the nucleic acids of the present invention can be in a host capable of expressing the antigenic polypeptide fragments contemplated by the present invention.

There are numerous *E. coli* expression vectors known to one of ordinary skill in the art useful for the expression of the antigen. Other microbial hosts suitable for use include bacilli, such as *Bacillus subtilis*, and other Enterobacteriaceae, such as Salmonella, Serratia, and various Pseudomonas species. In these prokaryotic hosts, one can also make expression vectors, which will typically contain expression control sequences compatible with the host cell (e.g. an origin of replication). In addition, any number of a variety of well-known promoters will be present, such as the lactose promoter system, a tryptophan (Trp) promoter system, a beta-lactamase promoter system, or a promoter system from phage lambda. The promoters will typically control expression, optionally with an operator sequence, and have ribosome binding site sequences for example, for initiating and completing transcription and translation. If necessary, an amino terminal methionine can be provided by insertion of a Met codon 5' and in-frame with the antigen. Also, the carboxy terminal extension of the antigenic fragments can be removed using standard oligonucleotide mutagenesis procedures.

Additionally, yeast expression can be used. There are several advantages to yeast expression systems. First, evidence exists that. proteins produced in a yeast secretion system exhibit correct disulfide pairing. Second, posttranslational glycosylation is efficiently carried out by yeast secretory systems. The Saccharomyces cerevisiae pre-pro-alpha-factor leader region (encoded by the Mfα-1 gene) is routinely used to direct protein secretion from yeast. The leader region of pre-pro-alpha factor contains a signal peptide and a pro-segment which includes a recognition sequence for yeast protease encoded by the KEX2 gene; this enzyme cleaves the precursor protein on the carboxyl side of a Lys-Arg dipeptide cleavage-signal sequence. The antigen coding sequence can be fused in-frame to the pre-pro-alpha-factor leader region. This construct is then put under the control of a strong transcription promoter, such s the alcohol dehydrogenae I promoter or a glycolytic promoter. The antigen coding sequence is followed by a translation termination codon which is followed by transcription termination signals. Alternatively, the antigen coding sequences can be fused to a second protein coding sequence, such as Sj26 or β glactosidase, used to facilitate purification of the fusion protein by affinity chromatography. The insertion of protease cleavage sites to separate components of the fusion protein is applicable to constructs used for expression in yeast.

Mammalian cells permit the expression of proteins in an environment that favors important post-translational modifications such as folding and cysteine pairing, addition of complex carbohydrate structures, and secretion of active protein. Vectors useful for the expression of antigen in mammalian cells are characterized by insertion of the antigen coding sequence between a strong viral promoter and a polyadenylation signal. The vectors can contain genes conferring either gentamicin or methotrexate resistance for use as selectable markers. The antigen and immunoreactive fragment coding sequence can be introduced into a Chinese Hamster ovary cell line using a methotrexate resistance-encoding vector. Presence of the vector DNA in transformed cells can be confirmed by Southern analysis and production of a cDNA or opposite strand RNA corresponding to the antigen coding sequence can be confirmed by northern analysis. A number of other suitable host cell lines capable of secreting intact proteins have been developed in the art and include the CHO cell lines, HeLA cells, myeloma cell lines, Jurkat cells, etc. Expression vectors for these cells can include expression control sequences, such as origin of replication, a promoter, an enhancer, and necessary information processing sites, such as ribosome binding sites, RNA splice sites, polyadenylation sites, transcriptional terminator sequences. Preferred expression control sequences are promoters derived from immunoglobulin genes, SV40, Adenovirus, Bovine Papilloma virus, etc. The vectors containing nucleic acid segments of interest can be transferred into the host cell by well known methods which vary depending on the type of cellular host. For example, calcium chloride transfection is commonly utilized for prokaryotic cells, whereas calcium phosphate treatment or electroporation may be used for other cellular hosts.

Finally, Baculovirus can be used to express recombinant proteins in insect cells.

Alternate vectors for the expression of antigen in mammalian cells, those similar to those developed for the expression of human gamma interferon, tissue plasminogen activator, clotting factor VIII, hepatitis B virus surface antigen, protease Nexinl and eosinophil major basic protein, can be employed. Further, the vector can include CMV promoter sequences and a polyadenylation signal available for expression of inserted nucleic acid in mammalian cells (such as COS7).

The nucleic acid sequences can be expressed in hosts after the sequences have been operably linked to , i.e., positioned to ensure functioning of, an expression control sequence. These expression vectors are typically replicable in the host organisms either as episomes or as an integral part of the host chromosomal DNA. Commonly, expression vectors can contain selection markers, e.g. tetracycline resistance or hygromycin resistance, to permit detection and/or selection of those cells transformed with the desired nucleic acid sequences (See U.S. Pat. No. 4,740,362; herein incorporated by reference).

Polynucleotides encoding a variant polypeptide may include sequences that facilitate transcription (expression sequences) and translation of the coding sequences such that the encoded polypeptide product is produced. Construction of such polynucleotides is well known in the art. For example, such polynucleotides can include a promoter, a transcription termination site (polyadenylation site in eukaryotic expression hosts), a ribosome binding site, and optionally, an enhancer for use in eukaryotic expression hosts, and optionally, sequences for replication of a vector.

The turkey astrovirus of the present invention can also be used to produce reagents useful in other methods for detecting the presence of avian astroviruses. One example of a method for detecting avian astrovirus is through the use of antibodies specifically reactive to a conserved antigen as defined herein. A tissue or fluid sample can be contacted with an amount of an antibody, either polyclonal or monoclonal. The reaction is detected with the antigen. It is contemplated that the antigen will be intact cells containing the antigen or will be fragments of the antigen. As contemplated herein, the antibody includes any ligand which binds the antigen, for example, an intact antibody, a fragment of an antibody or another reagent that has reactivity with the antigen. The fluid sample of this method can comprise any body fluid which would contain the antigen or a cell containing the antigen, such as, for example, blood, plasma, serum, saliva, feces, and urine.

Enzyme immunoassays such as immunofluorescence assays (IFA), enzyme linked immunosorbent assays (ELISA), and immunoblotting can be readily adapted to accomplis the detection of the antigen. An ELISA method effective for detection of the antigen can , for example, be as follows: (1) bind the antibody to a substrate; (2) contact the bound antibody with the sample containing the antigen, (3) contact the above with a secondary antibody bound to a detectable moiety (e.g., horseradish peroxidase enzyme or alkaline phosphatase enzyme); (4) contact the above with the substrate for the enzyme; (5) contact the above with a color reagent; (6) observe the color change. The above method can be readily modified to detect antibody as well as antigen.

Another immunologic method that can be useful for detecting avian astrovirus utilizes monoclonal antibodies (Mabs) for detection of antibodies specifically reactive with avian astrovirus antigens. Sample from the test subject is reacted with the antigen bound to a substrate (antigen antibody complex) (e.g., 96 well plate). Excess sample is thoroughly washed from away. A labeled (enzyme-linked, fluorescent, radioactive, etc.) Monoclonal antibody is then reacted with the previously reacted antigen antibody complex. The amount of inhibition of monoclonal antibody binding is measured relative to a control. The degree of monoclonal antibody inhibition is a very specific test for a particular variety or strain since it is based on monoclonal antibody binding specificity. Mabs can also be used for detection directly in cells by IFA.

A micro-agglutination test can also be used to detect the presence of avian astroviruses. Latex beads (or red blood cells) are coated with the antigen and mixed with a sample, such that antibodies in the sample are specifically reactive with the antigen cross-link with the antigen, causing agglutination. The agglutinated antigen-antibody complexes form a precipitate, visible to the naked eye or capable of being detected b a spectrophotometer. In a modification of the above test, antibodies specifically reactive with the antigen can be bound to the beads and the antigen in the sample thereby detected.

In addition, as in a typical sandwich technique, the antibody can be bound to a substrate and reacted with antigen. Thereafter, a secondary labeled antibody is bound to epitopes not recognized by the first antibody and the secondary antibody is detected. Since the present invention provides avian astrovirus antigen for the detection of infectious avian astrovirus, other serological methods such as flow cytometry and immunoprecipitation can also be used as detection methods.

Figure 2A:
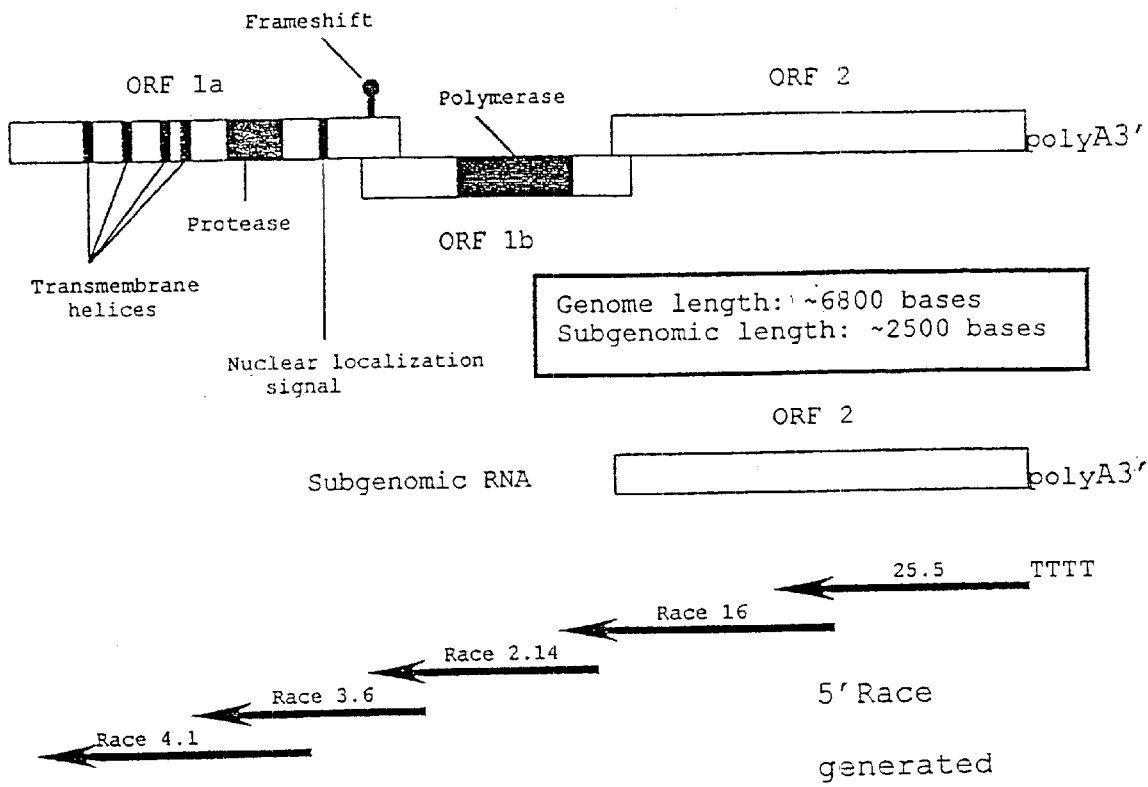
FIGS. 2A and 2B are diagrams of the astrovirus genomic organization.

In the diagnostic methods taught herein, the antigen can be bound to a substrate and contacted with a sample. This sample can be taken directly from the bird or in a partially purified form. In this manner, antibodies, specific for the antigen (the primary antibody) will specifically react with the bound antigen. Thereafter, a secondary antibody bound to, or labeled with, a detectable moiety can be added to enhance the detection of the primary antibody. Generally, the secondary antibody or other ligand which is reactive, either specifically with a different epitope of the antigen or nonspecific ally with, the ligand or reacted antibody, will be selected for its ability to react with multiple sites on the primary antibody. Thus, for example, several molecules of the secondary antibody can react with each primary antibody, making the primary antibody more detectable.

The detectable moiety will allow visual detection of a precipitate or a color change, visual detection by microscopy, or automated detection by spectrometry, radiometric measurement, or the like. Examples of detectable moieties include fluorescein and rhodamine (for fluorescence microscopy), horseradish peroxidase (for either light or electron microscopy and biochemical detection), biotin-streptavidin (for light or electron microscopy) and alkaline phosphatase (for biochemical detection by color change). The detection methods and moieties used can be selected, for example, from the list above, or other suitable examples by the standard criteria applied to such selections (Harlow and Lane, Antibodies; A Laboratory Manual, Cold Spring Harbor Laboratory, Cold Spring Harbor, N.Y., 1988; herein incorporated by reference).

The antigen of this invention can be used in the construction of a vaccine comprising an immunogenic amount of the antigen and a pharmaceutically acceptable carrier. The vaccine can be the entire antigen, the antigen on an intact turkey astrovirus, *E. coli*, or other strain, or an epitope specific to the antigen. The vaccine can also be potentially cross-reactive with antibodies to other antigens. The vaccine can then be used in a method of reducing and or preventing complications of avian astrovirus infection.

Immunogenic amounts of the antigen can be determined using standard procedures. Briefly, various concentrations of a putative specific immunoreactive epitope are prepared, administered to a bird, and the immunological response (e.g., the production of antibodies) of a bird to each concentration is determined.

The pharmaceutically acceptable carrier can comprise saline or other suitable carriers (Arnon, R. (ed) Synthetic Vaccines I. 83–92, CRC Press, Inc., Boca Raton, Fla. 1987). An adjuvant can also be a part of the carrier of the vaccine, in which case, it can be selected by standard criteria based on the antigen used, the mode of administration and the subject (Arnon, 1987; supra). Methods of administration can be by oral or sublingual means, or by injection, depending on the particular vaccine used and the subject to whom it is administered.

It can be appreciated from the above that the vaccine can be used as a prophylactic or therapeutic modality. Thus, the invention provides methods of preventing, reducing and/or treating avian astrovirus infection and the associated diseases by administering the vaccine to a subject.

The following examples are intended to further illustrate the invention and are not intended to limit the scope of the invention as described by the claims.

EXAMPLE 1

Turkeys having enteritis, high mortality, growth depression, lymphoid atrophy, and immunosuppresion were used to obtain infectious compositions. Thymus from turkey poults exhibiting diarrhea were homogenized in phosphate-buffered saline (PBS) in a Dounce homogenizer, and clarified by low speed centrifugation from about 500 to about 2,000 rpm. Supernatant was passed through a Whatman GD/×0.2 μm stacked filter (Fisher Scientific, Norcross, Calif.). Filtrates were inoculated into the yolk sac of 20-day-old specific pathogen free (SPF) turkey embryos. Eggs were incubated for about 5 days at about 37° C. to about 390° C. After the incubation period, intestines, intestinal fluid, and bursas were removed. Pools of embryo tissue were homogenized and filtered as above and passed through embryos a total of about three times.

After final passage, embryo intestines, fluid, and bursas were homogenized, clarified and filtered as above again. The filtrate was centrifuged in a Sorvall fixed angle rotor for about 3 hours at about 23,435×g. Supernatant was removed and the viral pellet was resuspended in about 1 milliliter of approximately 0.5 M Tris-0.25 M EDTA (TE) buffer, about pH 7.0. The suspension was overlaid on about a 27%/37% CsCl gradient and centrifuged (L8–60M Ultracentrifuge, Beckman) for about 15 hours at about 22,000 rpm in a SW28 rotor (Beckman). After centrifugation, a faint band was visible above the gradient layer, which was removed with a syringe in a total volume of about 3 milliliters. The extracted band was diluted to about 15 milliliters in TE buffer and centrifuged again at about 23,425×g for about 3 hours in a fixed angle rotor. The supernatant was removed and the rinsed pellet was resuspended in about 200 μl of PBS to form a purified infectious composition.

Approximately 50 μl of the purified infectious composition was negatively stained (Hayat et al., Negative Staining, McGraw-Hill Publishing Co., 1990; herein incorporated by reference in its entirety)and analyzed by transmission on a JEM-1210 Transmission Electron Microscope (JEOL, Inc., Tokyo, Japan) (FIG. 1).

EXAMPLE 2

Total RNA was isolated (Chomczynski et al., Anal. Biochem., Volume 162, 156–159, 1987; herein incorporated by reference) from the purified virus, obtained in Example 1, using TRIzol® Total RNA Reagent (Life Technologies™, Rockville, Md.). An initial cDNA library was synthesized (Gubler et al., Gene, Volume 25, 263–269, 1983; herein incorporated by reference) using the SMART cDNA Library Construction Kit (Clonetech Laboratories, Inc.™, Palo Alto, Calif.) and then cloned using the TOPO-XL cloning system (Mead et al., Bio/Technology (N.Y.), Volume 9, 657–663, 1991; herein incorporated by reference) according to manufacturer's directions (Invitrogen, San Diego, Calif.). Clones were screened using Luria-Bertani medium containing kanamycin (Hanahan et al., In. D. M. Glover (ed.) DNA, Cloning, Volume I: A Practical Approach, 366–369, 1985, IRL Press, Oxford, United Kingdom; Herein incorporated by reference).

Approximately 25 clones, of varying length, were sequenced as previously described (Seal et al., J. Clin. Microbiol., Volume 365, 1141–1145, 1998; Herein incorporated by reference) and analyzed using DNASTAR (Madison, Wis.) and GeneWorks 2.3 (IntelliGenetics, Mountain View, Calif.) programs. These sequences were compared to reported sequences in the GenBank database using the basic local alignment search tool (BLAST) (Altschul et al., J. Mol. Biol., Volume 215, 403–410, 1990; Herein incorporated by reference), and phylogenetic analysis was completed using parsimony (Swofford, PAUP:Phylogenetic analysis using parsimony, 4.0 ed., Illinois Natural History Survey, Champaign; Herein incorporated by reference). Two clones (p25.5 and p25.6) were identified as having putative amino acid similarities to TAstV and HAstV capsid protein (FIG. 2A). These clones represented the approximately last 1.5 kb of the 3' end of the astrovirus genome and contained the poly (A) tail. Gene-specific primers were created using PRIMER2 software (Scientific and Educational Software, Stateline, Pa.) and were used to synthesize a series of cDNA libraries using the 5' RACE system for rapid amplification of cDNA ends (Frohman, Methods in Enzymol., Volume 218, 340–356, 1993; Herein incorporated by reference) (Version 2.0, Life Technologies). Each cycle of subsequent cDNA synthesis was designed to overlap with its predecessor by at least 200 nt. FIG. 2A illustrates the astrovirus genome and the sequencing strategy used. Each new clone, upstream of the previous sequence, was analyzed by BLAST individually. This was undertaken to reduce the chance of bias towards astrovirus when incorporated into the growing consensus data. Three or more clones from each 5' Race reaction were sequenced at least three times to generate one overall consensus sequence for TAstV. Finally, RNA was isolated from the intestines of experimentally infected turkey poults, and TAstV was resequenced directly from the RT-PCR product. Briefly, about 1 µg of total RNA was incubated with about 20 pmol of each deoxynucleoside triphosphate, and about 15 U of Superscript Reverse Transcriptase (Life Technologies) in about a 20 µl reaction mixture for about 60 minutes at about 42° C. An aliquot (about 2 µl) of the first-strand product was amplified in about a 50 µl reaction mixture containing about 20 pmol of each of primers MKCAP8, MKCAP19, MKPOL10, MKPOL11; about 20 pmol of each deoxynucleoside triphosphate, about 1.5 mM $MgCl_2$, and about 1.5 U Tag polymerase (Life Technologies). Amplification was performed in a Perkin-Elmer 2400 DNA thermal cycler, and products were then purified using the Qia-quick PCR purification system (Qiagen, Valencia, Calif.) and sequenced. There was no significant difference between the sequence of the cloned cDNA and the RT-PCR products using primers of different distances from the suspected end (all of the primers used were within 1 kb of the suspected end). These products were electrophoresed in about a 1% agarose gel to confirm that each reaction yielded an amplicon of the expected size. These products were purified and sequenced as above.

Figure 2B:
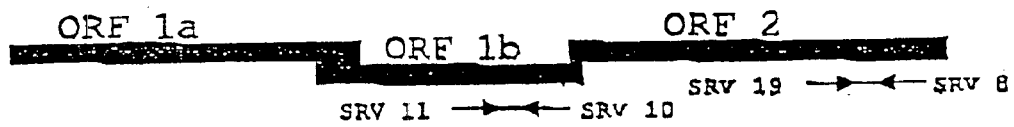

Analysis of the complete, 7,325-nt TAstV-sequence identified three ORFs (FIGS. 2A and 2B). These ORFs were identified by BLAST analysis as coding for astrovirus-like proteins and being in a similar gene order. Each of these ORFs and their predicted gene products were compared to the corresponding reading frame of previously reported astroviruses.

The predicted amino acid sequence of ORF2 was compared to the previously reported astrovirus capsid sequences (Table 1). TAstV was determined to be approximately 23.5% similar to the reported nucleotide sequence of TAstV-1.

However, only the last 476 nt of TAstV-1 have been published; therefore this comparison is limited to this extreme 3' end of the virus. When the predicted amino acid sequence of this region was compared to the sequence obtained, the turkey isolates were found to be about 21.9% similar. When the same region of the virus was compared with the mammalian isolates, TAstV was found to have a nucleotide similarity of about 22% and a predicted amino acid similarity of about 12% (Table 1). The same degree of similarity was observed between TAstV-1 and the mammalian isolates. In addition the mammalian isolates were determined to have nucleotide and amino acid similarities of about 23 to 58% and about 12 to 60%, respectively (data not shown).

Figure 3:
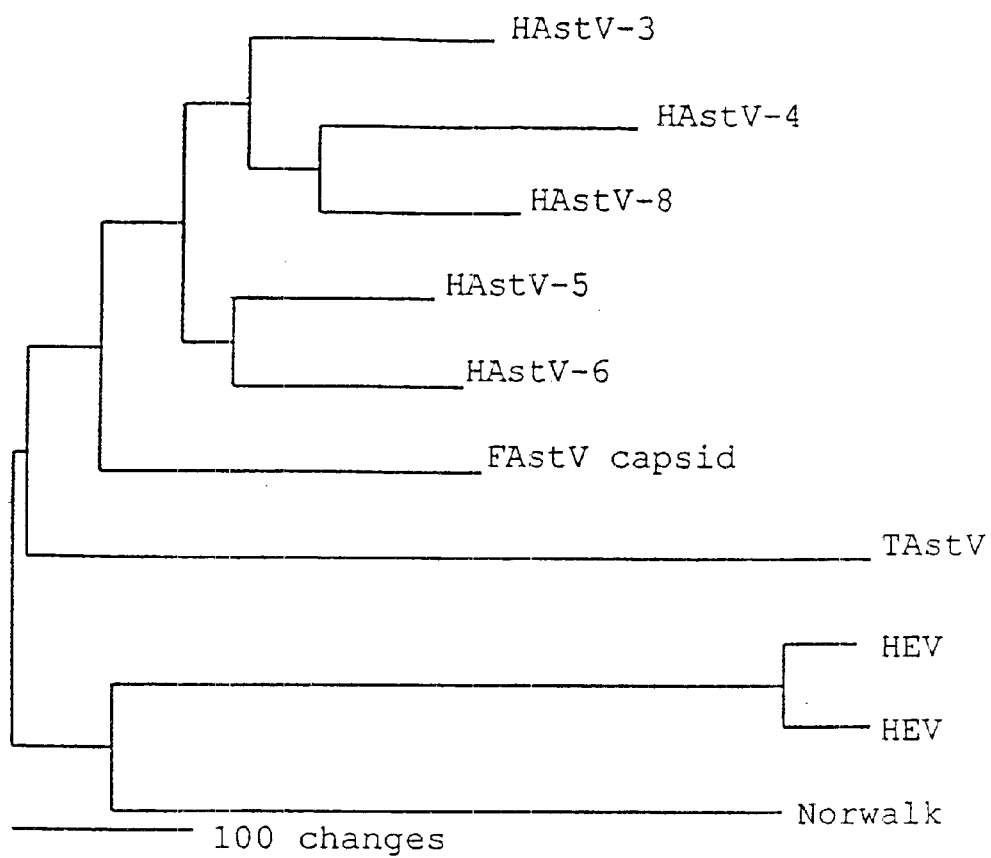
FIG. 3 shows phylogenic relationship of predicted capsid proteins from human astrovirus type 3 (HAstV-3), human astrovirus type 4 (HAstV-4), human astrovirus type 5 (HAstV-5), human astrovirus type 6 (HAstV-6), human astrovirus type 8 (HAstV-8), feline astrovirus (FAstV), turkey astrovirus (TAstV), Hepatitis E virus (HEV), and Norwalk virus.

The predicted amino acid sequence of the entire TAstV capsid protein was also compared to published astrovirus sequences. However, only the feline astrovirus (FAstV)and HAstV capsid proteins have been completely sequenced. These sequences were used to determine amino acid similarities (Table 1, below) and phylogenetic relationships (FIG. 3). Comparisons were done between the last 476 nt of each viral genome (column 2 of Table 1 below), the last 114 amino acids of the capsid protein from each virus (column 3 of Table 1 below), and the entire predicted amino acid sequence of the capsid protein (column 4 of Table 1 below). A heuristic search was completed with midpoint rooting. The phylogenetic tree in FIG. 3 shows that astroviruses clustered in one main branch, while the hepatitis E virus and Norwalk virus sequences clustered together as another branch.

The amount of similarity between the sequence of this turkey isolate and the mammalian sequences was not surprising, as avian viruses can be quite different from their mammalian counterparts. However, it was surprising at the limited similarity observed between this isolate and TAstV-1. The previously reported sequence was used by Jonassen et al. to identify a region conserved among astroviruses within the 3' noncoding sequence (Jonassen et al., J. Gen. Virol., Volume 79, 715–718, 1998). This conserved region was not identified in our isolate, and furthermore, primers designed from the conserved region failed to produce RT-PCR product from our isolate. The reason for this lack of similarity is not understood. However, TAstV may represent a different serotype since antibodies against the TAstV-1 isolate failed to recognize our virus by Western blot analysis (data not shown).

Figure 5:
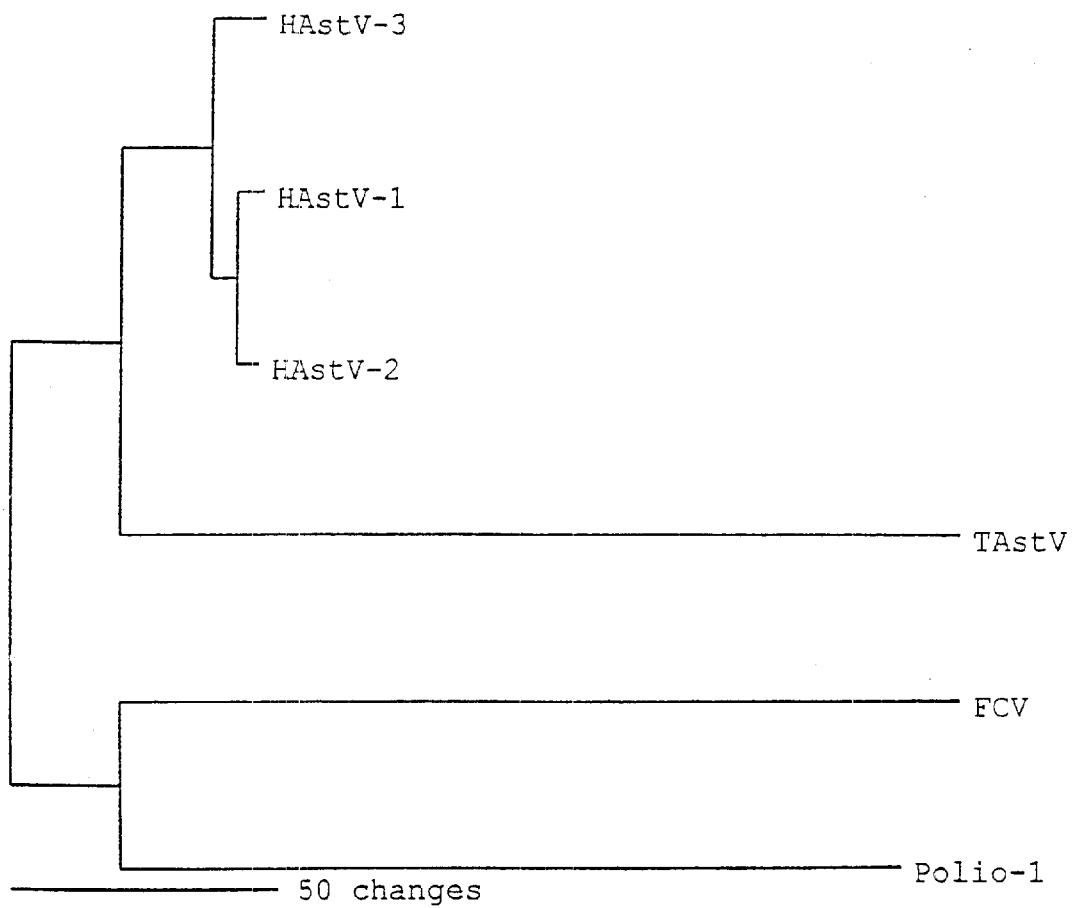
FIG. 5 shows phylogenetic relationship of the RDRP from astroviruses and representatives of other small round viruses. The amino acid sequence of feline calicivirus (FCV), human picornavirus (polio-1), and human astrovirus type-1 (HAstV-1), 2 (HAstV-2), and 3 (HAstV-3) were utilized to phylogenetically evaluate the putative turkey astrovirus (TAstV) polymerase.

Predicted amino acid sequence of ORF 1B indicated the presence of the viral RNA polymerase active-site motif YGDD (SEQ ID NO 64) (data not shown) (Ishihama et al., Arch. Virol., Volume 134, 235–258, 1994). The amino acid sequence of this putative polymerase was compared to the published astrovirus polymerase sequences. HAstVs are the only astroviruses completely sequenced; therefore, the TAstV polymerase sequence was aligned with the amino acid sequences of HAstV RDRPs (SEQ ID NO 65) (FIG. 4). The similarity between TAstV and the HAstV isolates varied from about 35% to about 38%. Phylogenetic analysis of the entire amino acid sequence of the polymerases of TAstV, HAstV-1, HAstV-2, and HAstV-3 were completed using a heuristic search with midpoint rooting (FIG. 5). The polymerase proteins from a representative of the picornavirus family (poliovirus type 1) and a representative of the calicivirus family (feline calicivirus [FCV]) were used for comparison. The TAstV isolate reported here groups most closely with the HAstV isolates compared with the other positive-sense RNA virus-type polymerases analyzed. TAstV ORF 1B showed the greatest similarity to HAstV compared to the other ORFs. This was expected, since RDRPs are well conserved proteins. The polymerase is the only highly conserved protein that is present in all positive-stranded RNA viruses; because of this they can be used to classify and separate related viruses (Koonin et al., Mol. Biol., Volume 28, 375–340, 1993 [Erratum Volume 28, 546]).

Analysis of ORF 1A identified a putative serine protease motif from the predicted amino acid sequence. This sequence was aligned with the serine protease sequences of HAstV types 1,2, and 3. As present in FIG. 6, there is sequence identity particularly around the proposed catalytic amino acids (Willcocks et al., J. Gen. Virol., Volume 75, 1785–1788, 1994). This position is occupied by the aspartic acid in the HAstV proteases. TAstV has the amide form of aspartic acid (asparagine) at position 40. Asparagine is less reactive than aspartic acid and is reported as a conserved substitution by BLAST analysis. TAstV does contain an aspartic acid residue in this region of the protein, at position 39 (FIG. 6). The reason for this mismatch is not understood; however, the putative catalytic histidine and serine residues of TAstV and HAstV are in alignment at position 7 and 104 (FIG. 6). Astrovirus is the only small, round, positive-sense RNA virus reported to code for a serine protease (Willcocks et al., 1994, supra). Both caliciviruses and picornaviruses are reported to code for a cysteine protease (Carter et al., Arch. Virol. Suppl., Volume 9, 429–439, 1994; Gorbalenya et al., FEBS Lett., Volume 243, 103–114, 1989).

Additional analysis of the TAstV genome revealed the presence of a possible frameshift sequence and secondary structure (FIG. 7) first described by Jiang et al. (Proc. Natl. Acad. Sci. USA, Volume 90, 10539–105343, 1993) in HAstV. The signal for this frameshift (AAAAAAU; SEQ ID NO 63) is similar to that of the retrovirus mouse mammary tumor virus (Brierley, J. Gen. Virol., Volume 76, 1885–1892, 1995; Jiang et al., 1993, supra). This sequence and structure are not found in other small, round RNA viruses and was one of the reasons for astrovirus classification in a family of its own (Jiang et al., 1993, supra; Monroe et al., J. Virol., Volume 67, 3611–3614, 1993).

Figure 8:
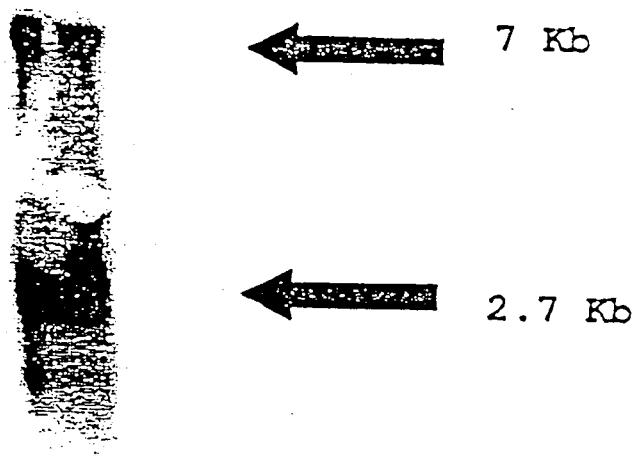
FIG. 8 shows a Northern blot hybridization of total RNA from astrovirus infected (Lane 2) and astrovirus uninfected (Lane 1) turkey embryo intestines. The PCR probe synthesized from clone 25.5 (FIG. 1) hybridized to a ~7 Kb genomic RNA and a ~2.7 Kb subgenomic RNA (Lane 2).

Finally Northern blot analysis was used to detect two viral RNA species, one of approximately 7 kb and one of approximately 2.7 kb (FIG. 8). This was done using total RNA from intestines of control SPF embryos (FIG. 8, lane 1) and total RNA from intestinal fluid of virus-inoculated SPF turkey embryos (FIG. 8, Lane 2). These RNAs were electrophoresed in a denaturing 1.2% agarose gel (Lehrach et al., Biochemistry, Volume 16, 4743–4751, 1977) and then transferred and cross-linked to nylon as described previously (Sambrook et al., Molecular Cloning, a Laboratory Manual, 2 ed., Volume 1, Cold Spring Harbor Laboratory Press, Cold Spring Harbor, N.Y., 1989). The RNA was then probed using a 392-bp double stranded DNA probe specific to base positions 588 to 979 of ORF 2. This probe was synthesized by PCR, using gene-specific primers, clone 25.5 (FIG. 2A) and digoxigenin-11-dUTPs and then hybridized to the membrane, and detected by chemiluminescence following the manufacturer's instructions (Roche Molecular Biochemicals, Indianapolis, Ind.). The detected RNAs correspond to the reported size of the astrovirus genome and subgenomic RNA (Jiang et al, 1993, supra). There is also a faint third band visible beneath the subgenomic RNA. The identity of this band is not known.

Synthesized cDNA was cloned using the TA cloning system (Mead et al., Biotechnology (NY), Volume 9, 657–663, 1991; herein incorporated by reference) according to the methods of the manufacturer (Invitrogen, San Diego, Calif.). Ligated cDNA was transformed into *E. coli* with standard transformation buffer and plated on media with kanamycin (Hanahan, DNA Cloning, Volume I, A Practical Approach, IRL Press, Oxford, 366–369, 1985; herein incorporated by reference).

TABLE 1

Pairwise similarities of HAstV isolates, FAstV, PastV, SAstV, previously reported TAStV sequence (TAstV-1), HEV, and Norwalk to the TAtV of the present invention.

| Virus | % Similar of last 476 nt | % similar of last 114 aa | % similar of predicted protein |
|---|---|---|---|
| HAstV-1 | 22.9 | 11.4 | 17.4 |
| HAstV-2 | 23.3 | 12.3 | ND* |
| HAstV-3 | 26.5 | 12.3 | 18.1 |
| HAstV-4 | ND | 12.3 | 18.1 |
| HAstV-5 | 20.6 | 12.3 | 17.5 |
| HAstV-6 | 24.8 | 10.5 | 18.2 |
| HAstV-8 | 22.5 | 12.3 | 17.8 |
| FAstV | 22.9 | 16.7 | 18.1 |
| PAstV | 23.9 | 15.8 | NA# |
| SAstV | 20.4 | 12.3 | NA |
| TAstV-1 | 23.5 | 21.9 | NA |
| HEV | 20.8 | 8.8 | 11.4 |
| HEV | 23.5 | 9.6 | 11.2 |
| Norwalk | 20.2 | 10.5 | 11.1 |

*ND: This comparison was not done.
NA: Sequence information was not available for this comparison

EXAMPLE 3

To detect TAstV virus using RT-PCR, total RNA was isolated from the intestines of astrovirus inoculated and control specific pathogen free (SPF) turkey embryos, experimentally infected and sham infected turkey poult, as well as the intestines and feces from commercial turkey flocks suffering from enteric disease using the TRIzol® Total RNA Isolation Reagent (Life Technologies™, Rockville, Md.). First strand cDNA was synthesized by incubating about 1 µg of the extracted total RNA with about 20 pmol of reverse primer, MKCAP8 and MKPOL10, in about a 20 µl reaction containing about 15 units of Superscript Reverse Transcriptase (Life Technologies™), and about 20 pmol of dNTPs at about 42° C. for about 60 minutes. An aliquot of approximately 2 µl of the first strand product was used as template for amplicifation in about a 50 µl reaction containing approximately 10 pmol of primers MKCAP8 and MKCAP19 (FIG. 9A) or MKPOL10 and MKPOL11 (FIG. 9B), approximately 20 pmol of dNTPs, approximately 1.5 mM MgCl$_2$, and approximately 1.5 units of Taq DNA polymerase (Life Technologies ™). Amplification, performed in a Perkin-Elmer 2400 DNA thermalcycler, involved an initial denaturing step at about 94° C. for about 1 minute, followed by about 35 cycles of about 94° C. for about 30 seconds, 56° C. for about 30 seconds, and about 72° C. for about 1.75 minutes and finishes with a final extension set at about 72° C. for about 2.5 minutes. PCR products were electrophoresed in about a 1.1% agarose gel in TAE buffer and visualized by ethidium bromide staining and ultra violet irradiation (Sambrook et al., Molecular cloning: A laboratory Manual, Volume 1,. Cold Spring Harbor, Cold Spring Harbor; Herein incorporated by reference). The PCR products were purified by Qiaquick®, Valencia, Calif.) and sequenced (Smith et al., Nature, Volume 321 (6071), 674–679, 1986; Herein incorporated by reference) (Applied Biosystems) to confirm amplification of the intended gene (data not shown).

Using primer pair MCKAP8 and MKCAP19 (FIG. 9A), a 849 bp product was amplified from the total RNA from astrovirusinfected turkey poults from the laboratory model and from commercial turkey flocks which were suffering from enteric disease. There was no 849 bp PCR amplification product in the control SPF embryo and uninfected turkey poult reactions. The sequence of the field products were determined to be approximately 85% similar to the amplicon from the experimentally infected poults and SPF embryos (Data not Shown).

Figure 9A:
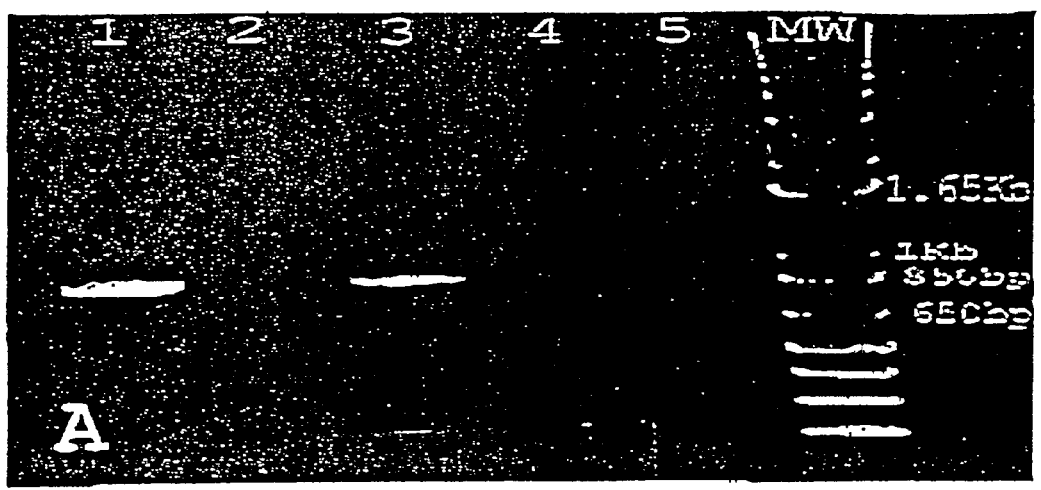
FIG. 9(A) shows RT-PCR product using primers MKCAP19 and MKCAP8 from the capsid region of TAstV. Lanes 1 and 3 show the presence of the approximately 879 bp capsid fragment. Lane 1: Inoculated embryo intestine. Lane 2: Control embryo culture. Lane 2: Infected turkey poult intestine. Lane 4: Non-infected turkey poult intestine. Lane 5: No template primer control.
Figure 9B:
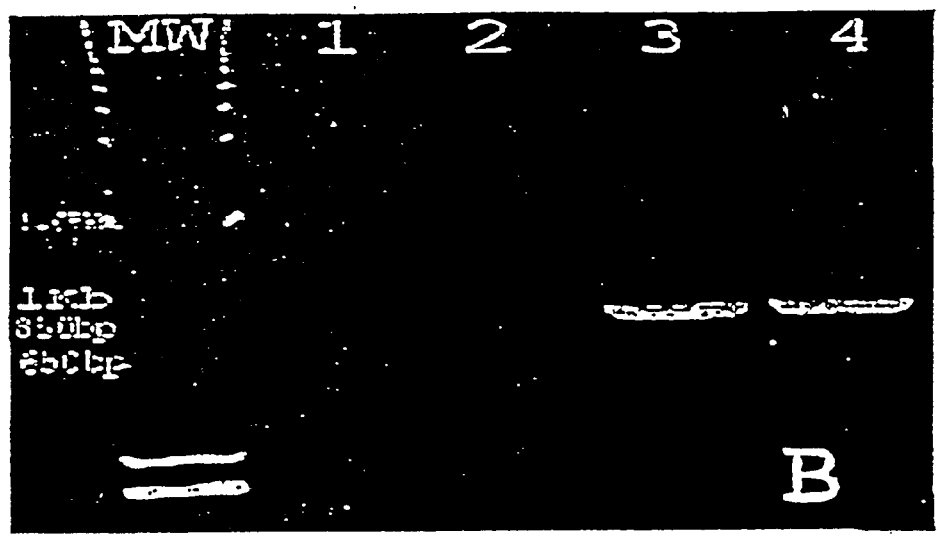
FIG. 9(B) shows detection of the approximately 802 bp polymerase fragment of TAstV, using primers MKPOL10 and MKPOL11. Lane 1: No template primer control. Lane 2: Control embryo intestine. Lane 3: Inoculated embryo intestine. Lane 4: Infected turkey poult.
Figure 10A:
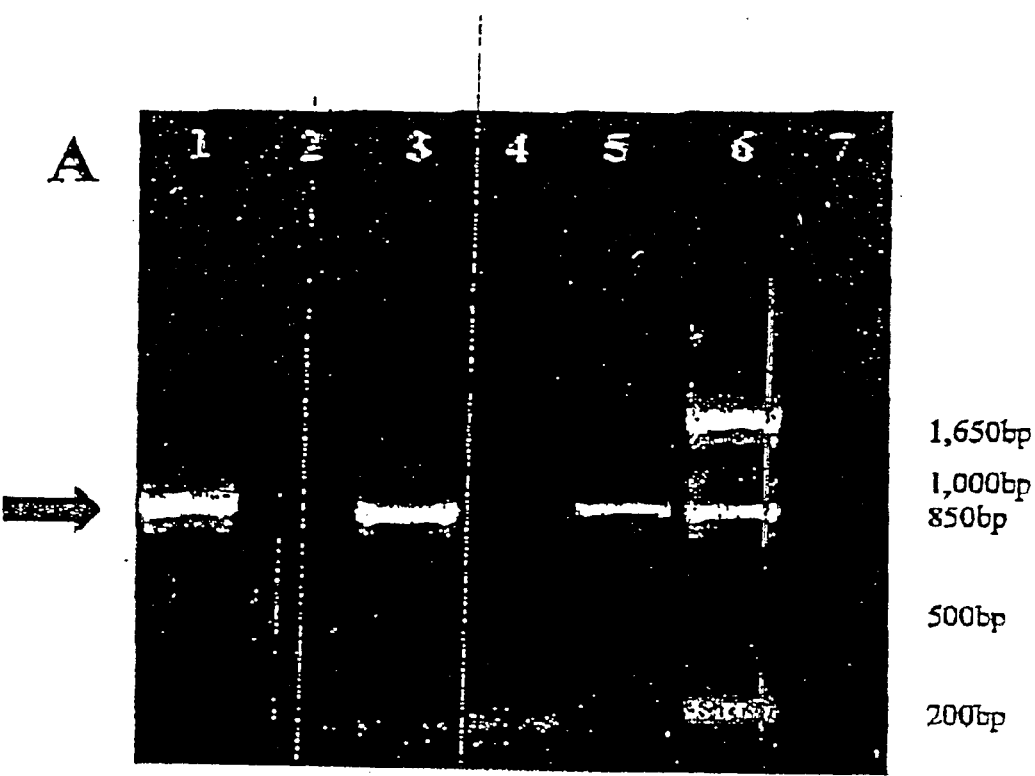
FIGS. 10A and 10B are gels showing amplification and detection of 849 bp amplicon from the capsid region of TAstV using primers MKCAP19 and MKCAP8 (A), and an 802 bp amplicon form the TAstV polymerase gene using primers MKPOL10 and MKPOL11 (B). Lanes 1) TAstV inoculated SPF turkey embryo intestine; 2) Control SPF turkey embryo intestine; 3) experimentally infected turkey poult intestine; 4) Sham infected turkey poult intestine; 5) Intestine of turkey poult from field flock with enteritis; 6) Feces of turkey poult from field flock with enteritis; 7) no template.
Figure 10B:
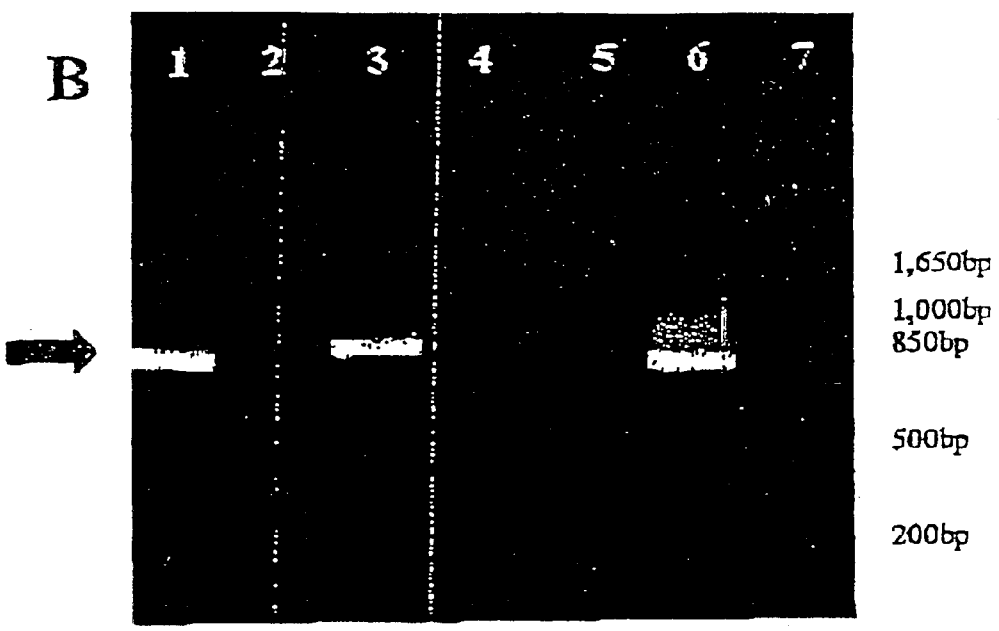
Figure 11A:
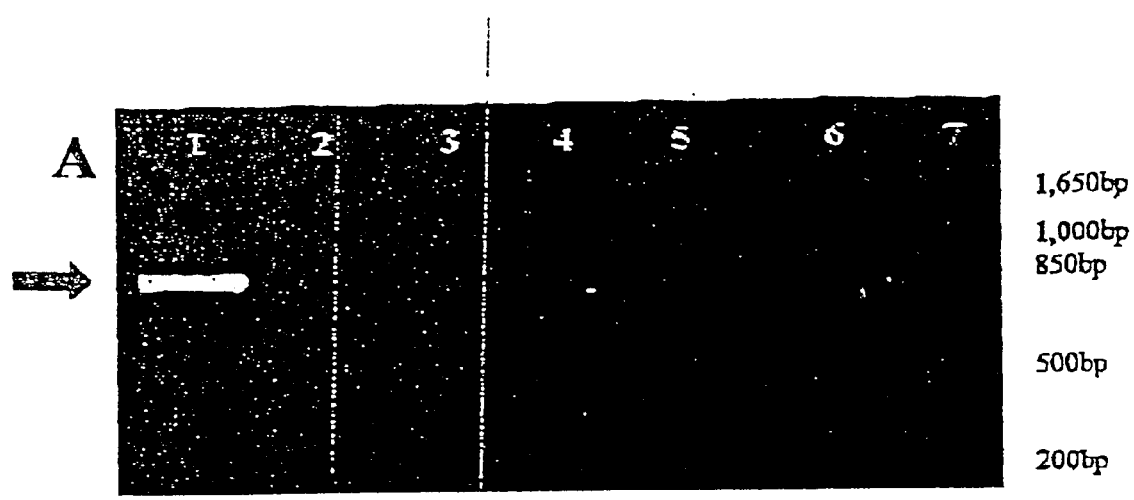
FIGS. 11A and 11B are gels showing specificity of TAstV RT-PCR. Lanes 1) Astrovirus inoculated SPF embryo intestine; 2) Control SPF embryo intestine; 3) turkey coronavirus positive poult intestine; 4) avian encephalomyelitis virus; 5) avian nephritis virus; 6) bovine entrovirus; 8) goose parvovirus. Detection of 849 bp amplicon using primers MKCAP8 and MKCAP19 (A) and 802 bp amplicon using primers MKPOL10 and MKPOL11 (B) is only seen in inoculated SPF embryo intestine.
Figure 11B:
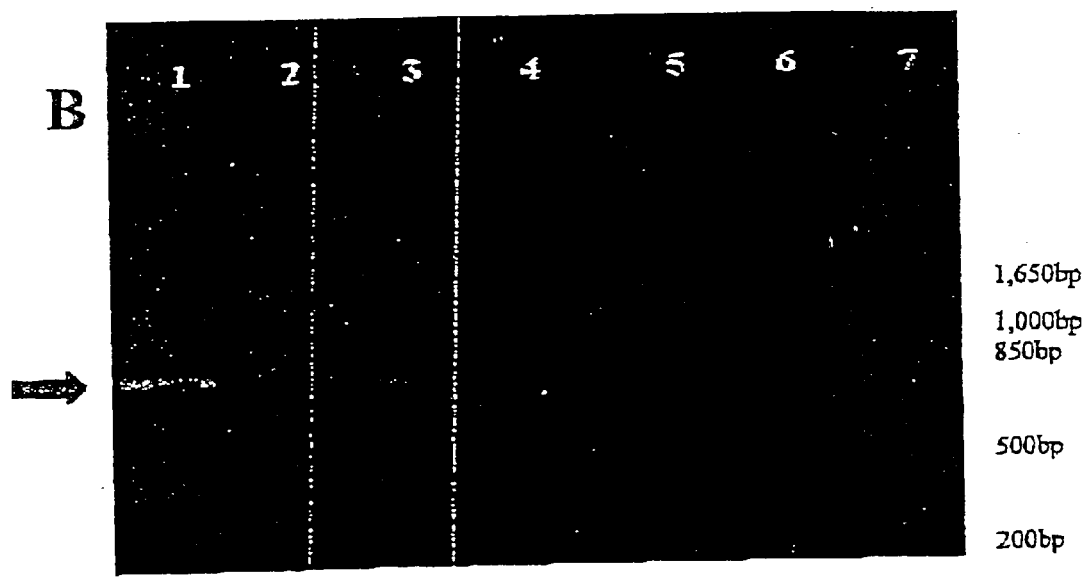

Because of possible immune pressures on the capsid gene, which could lead to multiple serotypes, primers were also designed to the viral polymerase gene. This gene is highly conserved (relative to the capsid gene) (Poch et al., Embo J., Volume 8 (12), 3867–3874, 1989). Primer set MKPOL10 and MKPOL11 produced an 802 bp amplicon in the astrovirus inoculated SPF embryo intestines, experimentally infected turkey poults, as well as from feces and intestines of enteric turkey flocks (FIG. 9B). The amplified product from the field samples were determined to be approximately 92% similar to the poults and SPF embryos infected experimentally (FIGS. 10A and 10B). Both of these primer sets were analyzed for their specificity to TAstV. Several viruses of enteric origin were used to examine cross-reactivity (FIGS. 11A and 11B). RNA was isolated, as described above, from the intestines of coronavirus positive turkey poults, avian encephalomyelitis virus (AEV), avian nephritis virus (ANV), and bovine entrovirus. In addition, DNA was isolated from goose parvovirus infected cells using DNAzol® Reagent Genomic DNA Isolation Reagent (Life Technologies™, Rockville, Md.). RT-PCR reactions were performed as described above, and PCR of goose parvovirus utilized the same conditions as the other viruses, however, about 100 ng of total DNA was used as the template for these reactions. FIG. 9A shows that the primers MKCAP8 an MKCAP19 only produced the expected 849 kb amplicon with the astrovirus inoculated SPF embryo intestines RNA. The same is true with primers MKPOL10 and MKPOL11 (FIG. 9B); the 802 kb amplification product is only detected in the astrovirus inoculated SPF embryo intestines. These data show these primers specifically detect the presence of TAstV.

The foregoing detailed description is for the purpose of illustration. Such detail is solely for that purpose and those skilled in the art can make variations therein without departing from the spirit and scope of the invention.

We claim:

1. An isolated turkey astrovirus having a nucleic acid sequence as set forth in SEQ ID NO: 1, or having a nucleic acid sequence which, as a result of the genetic code, is degenerate to SEQ ID NO:1.

2. An isolated nucleic acid sequence encoding open reading frame 1a of a turkey astrovirus having a sequence as set forth in the Sequence Listing as SEQ ID NO 62.

3. An isolated nucleic acid sequence encoding open reading frame 1b of a turkey astrovirus having a sequence as set forth in the Sequence Listing as SEQ ID NO 63.

4. An isolated nucleic acid sequence encoding open reading frame 2 of a turkey astrovirus having a sequence as set forth in the Sequence Listing as SEQ ID NO 3.

5. A vector comprising the nucleic acid of claims 2,3, or 4.

6. A method for detecting avian astrovirus comprising
   (a) isolating total RNA from a sample to be tested,
   (b) synthesizing a first strand DNA with SEQ ID NO:1 from said isolated total RNA using a reverse primer which is complementary to a portion of SEQ ID NO:1,
   (c) amplifying said first strand DNA using a primer from step (b) to form an amplified product, and
   (d) detecting the amplified first strand DNA product of step (c).

* * * * *

SEQUENCE LISTING

```
<160> NUMBER OF SEQ ID NOS: 65

<210> SEQ ID NO 1
<211> LENGTH: 7355
<212> TYPE: DNA
<213> ORGANISM: Turkey Astrovirus
<300> PUBLICATION INFORMATION:
<301> AUTHORS: Koci, Matthew D.
      Seal, Bruce S.
      Schultz-Cherry, Stacey
<302> TITLE: Turkey Astrovirus polyprotein Gene, complete cds, RNA
      polymerase gene;   partial cds;  and capsid protein
      gene, complete cds
<308> DATABASE ACCESSION NUMBER: GenBank
<309> DATABASE ENTRY DATE: 2000-03-29

<400> SEQUENCE: 1
ccgaaagtgt tgtcggggcg atggcccagg cgggtcgcag tggcgatgct tttgcatccc      60
ttgatcaacg gcgggagcgc caagaagaac aggcgcagtc cggccttgac aaggtgttct     120
acttccaagg cgtggttgaa ctattcaacc gtatgaaaat cgcctatgga aggacaccgg     180
cttggacggc cctcatgaag tgtaacgcca tatacttgaa agattttaaa acagcagttg     240
gcgttgaggg tacccgctat gggctctttt tcgcagaaga agtgactaaa ccaacttggt     300 caccgacat tggagcaaac ttgataactt tgggcgaaaa ggcctgttta gacgcccaaa      360
atgcaaaata tgaaagattg caagcctcac ttaaaacaac tagtggcctt gtgcatcaag     420
tgatggaaaa aactagggaa gctaaagaga acctagagaa agccaataag atccaagagc     480
aacttgacaa ggtcattgag agcaacaaag ctttacaccg taagatacag gagagaaacc     540
gagaaaagat gcaggaatac atggtaaggt tgcataacac gcagaaagat cgtgatgatt     600
gggttcagag atgctccagg ttagaacagg agaatgtcac attgcagaaa aggttgaagg     660
agaaagagaa cgcgctggta tctgttgggt gggatctttt aggctggata gttatttcag     720
tgcttgtatt cggcctgatt tcactcgcag acgcgcaaaa cttgactcca ccagccaaga     780
ttgtgataac tccagggcaa gcagagttca tggacctagc taaattggaa aaaatccagg     840
tcagaaagta ccgactggat agttgtgaat taccacctga gaaaggttgc gtgttgtaca     900
```

```
aggattacct taccaccagg ccggtaagct ttttggagtt gatggccaaa tgttcaaaac    960
ctgactgggt ctcggagagc agttacaatg aaacaaccct aatggaagaa tgcatccaga   1020
tctttggtgc agagtggtgt gaagggaagc tcgttgatct tgtaccaaga aagtgtggcg   1080
tctttggtgc agsgtggtgt gaagggaagc tcgttgatct tgtaccaaga aagtgtggcg   1140
ttatststgg taaggtgatg tcatacaggc tagatatgtg gataacatct atttttagtt   1200
tagttttggc aggtaataag gaaaaattgt ttaaaatggc tcccttcatt tttgtagcat   1260
ggtttttaaa cataccagtg ttttaacttt gtgtggcagt caacattttt ccagttgttt   1320
ccctgccttt cattttgttc cagattttta tgccacagtt tgttttggta aatgcctttc   1380
ttctatggtt aacactcact ttaacagcat tttattggag tgaggggccc aaaatactga   1440
tggagataag ttatgccctt gtgtatacca tcggctttgt tttatggtcc cttggactag   1500
ctgtggggt gacgctcaaa ttgacaatgg tacatcagat attaatgttt tgtgttgttg   1560
ccgcagctat ttgcggaacc aagtttgcat gcacaacaat aacagtgcaa cacccagatg   1620
gaacaaccgc aaaatacacc cgggttggta agctaaagaa taatgttgtg aaccagtgca   1680
aaaggtagt cacgacattg cagacaagag gcgttatacc agcaacgcct gcgaaaacag   1740
catctattgt tattgttgag ggcaaaaatg aacaggtgt tgggttcagg tttatgaatt   1800
atattcttac agcagaacac gtggttcagg gatcagatat agcaacactt aaaaatggca   1860
gtgttagtgt gaaatccaaa gtcatcaaaa cgatcccaat atttgagagt gttgacaatg   1920
ttgcagtgtt aaaattgcca cctgagctca atagcgtgaa gcctatcaaa ttagcaaaga   1980
aggttcaaag tgactatctg acactgacag cctatgatcc aaattttcaa catgccgcca   2040
cttttaccgg gtggtgtatt atagatggaa attggcttaa taactccttt gatacaaaat   2100
ttgggaatag tggtgcacct tattgtgatc atgatggtag gctagttggt atccacctag   2160
gcacacaggg tgttctttcc caaggcatag tcattgtaga cgcattgaaa aatacattcc   2220
agcttgcgga tcagtgtaga ccacagaatt ttgacatgga tgagttcctt gagaaagtta   2280
tagcaggaac aaaagtgtca catgcagcga tcctaaaaga actggaagaa cttagagaag   2340
aggtgcaatt tttaaagaaa aaatgtgtca cctatgatga ctactggcta tgccaaacca   2400
tctttgggca ggccaaaggg aagacgaaga aaacagtcag aggccgtaaa caccttgtta   2460
ccaaaagagc tcttgggaaa ggccacttca tgaagatgag gatgctcact gatgaagaat   2520
atcagaatat gattgaaaag ggcttctcag cagaggaaat aagggaggca gtcaacgcac   2580
tccgagaaca agcatggctt aattattgta ttgataatga tgttgatgac gaaggtgagg   2640
aagattggta tgatgacatg gtagagacag atagagttaa ccaggagatc gatgaggcca   2700
tagagcgggc catggaagat cgtggtgagt tctaccagaa gaaatcccgc cttacctttg   2760
ttgaacaggc catgatgcat ttgattcaag tgagcaagga gagaagccag actgctaaac   2820
tagaagttca aaaggagaat gaagcccaac tagtgaagat gtttgagcgg tgtgtcacag   2880
atgagaatac acctgagggt accacctcta tagcggcttt gtccacagaa gatgatgtta   2940
ggcttgttga agggaaagtc attgatttca ccaaagcaaa gaacatccca gttgacgggg   3000
aaattaggag agagatcatc cctggaacaa atgtactga gatttccact ggacctgaaa   3060
ataagaagaa catattgaag aaaaaggata cacacatagc tgagggtaaa gttgaaacta   3120
agtcatcaca gcagccggtt gacgtcaagg atgataaacc cgtagccttg gaacaacgta   3180
agcctagagc ttgtaaatgg tgcggttcat cacagaaaca tgattaccgg gaatgtcggt   3240
```

-continued

```
ttcaacgtga aaaacgcttt tgtgtgtatt gtgcagctat gcactcaatg tttgagggcc      3300
atataagacc aatagagtgc actagttgca agaaaagttt ttcaggaatt gagaagttag      3360
aagatcatgt ggtcagtgga gagtgtcaaa aaaactaata gagggcctg tgacaacaaa       3420 ggcccctacc cccgtaccag attggcttaa atatttgca tgggaagatg acatattacc      3480
acctgaaggt aaaactgcct taccagaaaa tgttactcta attggacata taccagttga      3540
taagttggtc tcgcgcacca agaaagtcca ggatccatta ttaggccttg taacaccatg      3600
gaaacaagat atgtatgatt caacaacatg gactgtaaag gcttcaccca aaatgtttga      3660
gaaattccat taccacgacc cagttgactt tgtggaacag tatgctgagt ttgtgctgtt      3720
gtgtgacaat atggtgttga gagagcatga ctatatggca aatagcaaca tcacaccaat      3780
catgtcaaca gagaaaaatg tcaatagtac accagcatac ccaaaattcc aagcctatga      3840
cagcgaagcc gagtatttgg aagattgtgg gtggcaagag tacctggatg ttgtgtctga      3900
tccagaaact ataaatcgta gaccccctatg gtggtgcttc ctcaaaaatg aagttctcaa     3960
aagagagaaa attgaggaca gtgacattcg aatgatattg tgcaccgacc cgattttac      4020 caggattggg gctatgtttg agcaggatca gaacaacaga atgaaacaac agactgaaat      4080
aaggtctgca caggtcggat ggaccccctt tttcggcggc ttggatcgca gggttcgcag      4140
gttgtatggt gatggagata ggtattttgt tgagatggac tggacacggt atgatgggac      4200
tataccaaaa tcactatttt ggagaattag gcaaatcagg ttcttcttcc tccatgattc      4260
tcataagact ccaaagatgc ggcgcttgta caactggtat gtgaaaaatc tgttggaaaa      4320 aattattttta ttgccaactg gagaagtttt ccaggtcaag aaaggaaatc caagtggtca      4380
gttttcaaca actgtggata taatatgat caatgtctgg ctaacaacat ttgaggtttc       4440
atacctattt ttcaaacagc gtggtagact gccaacagag aaagagctgc aagagaactg      4500
ctccatgata tgctacgggg atgacagact tctttccatc cgtaaagggt ttgttgagta      4560
cgaacctgat acagtcattg atatgtacaa aaacatcttt ggaatgtggg tgaaaagaaa      4620
caacatcaaa atccaagata cacctgaagg gctctctttt tgtgggctta caatagtaaa     4680
atcaagtact ggtgcatatg ttggtgttcc aatgtgaac aaaatactgt caactttga      4740 aaatccagta cgtaggctac cagatgttga gtctctttgg ggtaaattgg tttccctgcg      4800
catattgtgt gaaaatgctc ccagcaatgt taaacacttt cttgatgagc agattagcaa      4860
tgttgaggag ttcgccgcca gagaaaacat acaacttcct gaggtcgggc ccgacttcta      4920
ttccagaata tggtgagagg aggaccgaaa gaagatggcg gcgatggccg acaaggtcgt      4980
tgtcaagaag acaactacaa ggcgcagggg caggagtaat tcccgctccc gtagcaggag      5040
taggagcagg agcagaacta aaaagacagt caaaattatt gagaaaaagc cagaaaaatc      5100
catcctaaag aaaattgatc aggctgaaag aagagatgca aaacagctta ggcggattcg      5160
taagaaagtg cagggaccgc cagtaaattc caggatgaca acagtagtca cacttggtca      5220
gataacaggc aataaagaca cacccctaga gcggaaacac aagtgctttc tgaatccgct      5280
gttgatgaag agtcaggaaa ctggtcaaac tgcaacaccc ttatctgtta gggcatccca      5340
atataatctg tggaagctat ccagactcca tgtcagactt ataccccttg caggaaaagc      5400
gaatattttg gggtcagtgg tgttcttaga tcttgaacag gaggcaaaca cagcaggacc      5460
agaatcagta gataccatca aggcaagacc ccatgttgaa gttccatag ggtcgaaaac      5520 cgtttggaaa gtgcacccta gaagcgctct aggacctaga caggggtggt ggaatgttga      5580
ccctggtgac agcccaactg attctcttgg gccagcactc aacatgtgga cctacctgca      5640
```

```
aactgtcaat gcactccaga gcgctggggg cactcaaacg ccttacacca gtgcactttt    5700
tcttgtggag gtcttggtca cttatgagtt ttcaaactat ggcccaaagc ctgcactgtc    5760
tcaaatggta tcagacagct ttccaccagc ctccggttct actgcaacct taaaaaacac    5820
cagtgatggg gctgtagcaa tacaactctc aggcgctatc gcccgaaaga tggaggaggt    5880
tgagcccaag ggtaggcgct caaatgcgca acatcaggt gtcggtgaag tgttctgggc     5940
agtgtccact gaagtagtca atacagtagc agatgccata ccaggctggg gctggctcct    6000
gaaaggtggc tggtttgtcc ttaggaaaat ctttggggcc gcaaatgacc agaatggcac    6060
ttacttgata tactcttcag tggcagatgc acaaggtgac aacaggatat acacatcagt    6120
gaaacagaca cagttgacat caagcaggat caacctcgtc caactcaccc agcccaatgt    6180
gaaccaagca gcagtaggtg gcagtgttgg tgcggcaaac tccatctatt tgccactacc    6240
acaagcagat gaccaataca caccctactt tgtctataat tttcaagggg aaagggtgtc    6300
aaccaccgag actggggtat tttgtctggc agccatacca gctgcgacta catctagtag    6360
gtataataat cagatcacca ctccatcaat tggctacagg aatgctagtg gtacaggaac    6420
atcattccta ctagatgctg catcatggtg gaatatattg gatgtaactc agactggagt    6480 gcttttttgga caaccaagat tgggtgttgg tgtcatgcag acaatgaaga ctctcaaaca    6540
gcatatcaag gattacacag agcctgcaat acagaaatat tatcctggaa caactaacct    6600
tgatgagcag ttgaagcaga gattgaacct ggcagagggt gacccggtca tctcaatggg    6660
ggacacaaac ggtaggaggg ctgcactctt ttataggact agtgatgaaa aatatatttt    6720 attttttctca accacagaag atccagggc acagtatcaa aatctgaaaa tgttgtactt    6780
ctggaactgg tcctattctg acacaaaaca gcaatttttg gaccaccta gaacagtgca    6840 gtttgcaaat ttggatgaca gccagccagc cccctatgat agtgatgatg atgacctttc    6900
tgatgtaaca tcacttttg agcaggctga tttgggggat gagacagact tcaaatttaa    6960
tatgtccatc caaacctcca aacatcttga ggaggagaaa aattactgga aaaaccagtg    7020
tgagaggatg atgatggaga aggcccttttc gggcacctca cagcctcttg tccggtttga    7080
gaaagctgga cctagggcag accaatcttc tgccagtggt cattcttgaa tggccacact    7140
ttctctgcgg tggaaatgga aatcaccatt ccacctaaga tgattagccg atccaacgga    7200
aatcacccgt tgggtggtgc gcggtttacg catcgggaaa tcaacccggt gtattacccg    7260
cacttccggc tcaacagttt tttaaaactg atataaattt atgaaaattt tattagcatt    7320
ttaagaaaaa aaaaaaaaa aaaaaaaaa aaaaa                                 7355
```

<210> SEQ ID NO 2
<211> LENGTH: 20
<212> TYPE: DNA
<213> ORGANISM: Turkey Astrovirus

<400> SEQUENCE: 2
tcatcatcct ctcacactgg                                                  20

<210> SEQ ID NO 3
<211> LENGTH: 20
<212> TYPE: DNA
<213> ORGANISM: Turkey Astrovirus

<400> SEQUENCE: 3
agcagcagta ggtggcagtg                                                  20

```
<210> SEQ ID NO 4
<211> LENGTH: 20
<212> TYPE: DNA
<213> ORGANISM: Turkey Astrovirus

<400> SEQUENCE: 4
tggcggcgaa ctcctcaaca                                              20

<210> SEQ ID NO 5
<211> LENGTH: 20
<212> TYPE: DNA
<213> ORGANISM: Turkey Astrovirus

<400> SEQUENCE: 5
aataaggtct gcacaggtcg                                              20

<210> SEQ ID NO 6
<211> LENGTH: 20
<212> TYPE: DNA
<213> ORGANISM: Turkey Astrovirus

<400> SEQUENCE: 6
aagcgctcta ggacctagac                                              20

<210> SEQ ID NO 7
<211> LENGTH: 20
<212> TYPE: DNA
<213> ORGANISM: Turkey Astrovirus

<400> SEQUENCE: 7
ggaggtcttg gtcacttatg                                              20

<210> SEQ ID NO 8
<211> LENGTH: 20
<212> TYPE: DNA
<213> ORGANISM: Turkey Astrovirus

<400> SEQUENCE: 8
gatagcgcct gagagttgta                                              20

<210> SEQ ID NO 9
<211> LENGTH: 31
<212> TYPE: DNA
<213> ORGANISM: Turkey Astrovirus

<400> SEQUENCE: 9
attgccgcgc cacacttcac cgacacctga t                                 31

<210> SEQ ID NO 10
<211> LENGTH: 20
<212> TYPE: DNA
<213> ORGANISM: Turkey Astrovirus

<400> SEQUENCE: 10
accagtgtga gaggatgatg                                              20

<210> SEQ ID NO 11
<211> LENGTH: 32
<212> TYPE: DNA
<213> ORGANISM: Turkey Astrovirus

<400> SEQUENCE: 11
tattgccgcg cccggacaag agactgtgag gt                                32
```

```
<210> SEQ ID NO 12
<211> LENGTH: 20
<212> TYPE: DNA
<213> ORGANISM: Turkey Astrovirus

<400> SEQUENCE: 12
agaatgacca ctggcagaag                                               20

<210> SEQ ID NO 13
<211> LENGTH: 31
<212> TYPE: DNA
<213> ORGANISM: Turkey Astrovirus

<400> SEQUENCE: 13
attgccgcgc tcatcatcc tctcacactg g                                   31

<210> SEQ ID NO 14
<211> LENGTH: 20
<212> TYPE: DNA
<213> ORGANISM: Turkey Astrovirus

<400> SEQUENCE: 14
tgttgaggag ttcgccgcca                                               20

<210> SEQ ID NO 15
<211> LENGTH: 20
<212> TYPE: DNA
<213> ORGANISM: Turkey Astrovirus

<400> SEQUENCE: 15
tggcggcgaa ctcctcaaca                                               20

<210> SEQ ID NO 16
<211> LENGTH: 20
<212> TYPE: DNA
<213> ORGANISM: Turkey Astrovirus

<400> SEQUENCE: 16
aataaggtct gcacaggtcg                                               20

<210> SEQ ID NO 17
<211> LENGTH: 20
<212> TYPE: DNA
<213> ORGANISM: Turkey Astrovirus

<400> SEQUENCE: 17
cgacctgtgc agaccttatt                                               20

<210> SEQ ID NO 18
<211> LENGTH: 20
<212> TYPE: DNA
<213> ORGANISM: Turkey Astrovirus

<400> SEQUENCE: 18
tccgctgttg atgaagagtc                                               20

<210> SEQ ID NO 19
<211> LENGTH: 20
<212> TYPE: DNA
<213> ORGANISM: Turkey Astrovirus

<400> SEQUENCE: 19
```

```
gactcttcat caacagcgga                                              20

<210> SEQ ID NO 20
<211> LENGTH: 20
<212> TYPE: DNA
<213> ORGANISM: Turkey Astrovirus

<400> SEQUENCE: 20
aactgttgag ccggaagtgc                                              20

<210> SEQ ID NO 21
<211> LENGTH: 20
<212> TYPE: DNA
<213> ORGANISM: Turkey Astrovirus

<400> SEQUENCE: 21
cagagattga acctggcaga                                              20

<210> SEQ ID NO 22
<211> LENGTH: 20
<212> TYPE: DNA
<213> ORGANISM: Turkey Astrovirus

<400> SEQUENCE: 22
ctgccaggtt caatctctgc                                              20

<210> SEQ ID NO 23
<211> LENGTH: 20
<212> TYPE: DNA
<213> ORGANISM: Turkey Astrovirus

<400> SEQUENCE: 23
agcagcagta ggtggcagtg                                              20

<210> SEQ ID NO 24
<211> LENGTH: 20
<212> TYPE: DNA
<213> ORGANISM: Turkey Astrovirus

<400> SEQUENCE: 24
cactgccacc tactgctgct                                              20

<210> SEQ ID NO 25
<211> LENGTH: 20
<212> TYPE: DNA
<213> ORGANISM: Turkey Astrovirus

<400> SEQUENCE: 25
tggtgttgag agagcatgac                                              20

<210> SEQ ID NO 26
<211> LENGTH: 20
<212> TYPE: DNA
<213> ORGANISM: Turkey Astrovirus

<400> SEQUENCE: 26
ggcctaataa tggatcctgg                                              20

<210> SEQ ID NO 27
<211> LENGTH: 20
<212> TYPE: DNA
<213> ORGANISM: Turkey Astrovirus

<400> SEQUENCE: 27
```

```
ttgagcggtg tgtcacagat                                              20

<210> SEQ ID NO 28
<211> LENGTH: 20
<212> TYPE: DNA
<213> ORGANISM: Turkey Astrovirus

<400> SEQUENCE: 28
atctgtgaca caccgctcaa                                              20

<210> SEQ ID NO 29
<211> LENGTH: 20
<212> TYPE: DNA
<213> ORGANISM: Turkey Astrovirus

<400> SEQUENCE: 29
cactgacagc ctatgatcca                                              20

<210> SEQ ID NO 30
<211> LENGTH: 20
<212> TYPE: DNA
<213> ORGANISM: Turkey Astrovirus

<400> SEQUENCE: 30
tggatcatag gctgtcagtg                                              20

<210> SEQ ID NO 31
<211> LENGTH: 20
<212> TYPE: DNA
<213> ORGANISM: Turkey Astrovirus

<400> SEQUENCE: 31
agccgatggt atacacaagg                                              20

<210> SEQ ID NO 32
<211> LENGTH: 20
<212> TYPE: DNA
<213> ORGANISM: Turkey Astrovirus

<400> SEQUENCE: 32
ccttgtgtat accatcggct                                              20

<210> SEQ ID NO 33
<211> LENGTH: 20
<212> TYPE: DNA
<213> ORGANISM: Turkey Astrovirus

<400> SEQUENCE: 33
tgtggcgagc aacatgtctt                                              20

<210> SEQ ID NO 34
<211> LENGTH: 20
<212> TYPE: DNA
<213> ORGANISM: Turkey Astrovirus

<400> SEQUENCE: 34
aagacatgtt gctcgccaca                                              20

<210> SEQ ID NO 35
<211> LENGTH: 20
<212> TYPE: DNA
<213> ORGANISM: Turkey Astrovirus
```

<400> SEQUENCE: 35
ggcaagcaga gttcatggac                                                  20

<210> SEQ ID NO 36
<211> LENGTH: 20
<212> TYPE: DNA
<213> ORGANISM: Turkey Astrovirus

<400> SEQUENCE: 36
ggtccatgaa ctctgcttgc                                                  20

<210> SEQ ID NO 37
<211> LENGTH: 20
<212> TYPE: DNA
<213> ORGANISM: Turkey Astrovirus

<400> SEQUENCE: 37
agtggccttg tgcatcaagt                                                  20

<210> SEQ ID NO 38
<211> LENGTH: 20
<212> TYPE: DNA
<213> ORGANISM: Turkey Astrovirus

<400> SEQUENCE: 38
gatgcacaag gccactagtt                                                  20

<210> SEQ ID NO 39
<211> LENGTH: 20
<212> TYPE: DNA
<213> ORGANISM: Turkey Astrovirus

<400> SEQUENCE: 39
cctcatgaag tgtaacgcca                                                  20

<210> SEQ ID NO 40
<211> LENGTH: 20
<212> TYPE: DNA
<213> ORGANISM: Turkey Astrovirus

<400> SEQUENCE: 40
cctgttcttc ttggcgctcc                                                  20

<210> SEQ ID NO 41
<211> LENGTH: 20
<212> TYPE: DNA
<213> ORGANISM: Turkey Astrovirus

<400> SEQUENCE: 41
ggagcgccaa gaagaacagg                                                  20

<210> SEQ ID NO 42
<211> LENGTH: 20
<212> TYPE: DNA
<213> ORGANISM: Turkey Astrovirus

<400> SEQUENCE: 42
aatatgatca atgtctggct                                                  20

<210> SEQ ID NO 43
<211> LENGTH: 20
<212> TYPE: DNA
<213> ORGANISM: Turkey Astrovirus -continued

<400> SEQUENCE: 43
ccmctvtggt ggtgcttcct                                              20

<210> SEQ ID NO 44
<211> LENGTH: 18
<212> TYPE: DNA
<213> ORGANISM: Turkey Astrovirus

<400> SEQUENCE: 44
ggcccgacyt caggaagt                                                18

<210> SEQ ID NO 45
<211> LENGTH: 25
<212> TYPE: DNA
<213> ORGANISM: Turkey Astrovirus

<400> SEQUENCE: 45
tcgttaatta accgaaagtg ttgtc                                        25

<210> SEQ ID NO 46
<211> LENGTH: 20
<212> TYPE: DNA
<213> ORGANISM: Turkey Astrovirus

<400> SEQUENCE: 46
gaaagtgttg tcggggcgat                                              20

<210> SEQ ID NO 47
<211> LENGTH: 25
<212> TYPE: DNA
<213> ORGANISM: Turkey Astrovirus

<400> SEQUENCE: 47
cggtgaattc ccgaaagtgt tgtcg                                        25

<210> SEQ ID NO 48
<211> LENGTH: 20
<212> TYPE: DNA
<213> ORGANISM: Turkey Astrovirus

<400> SEQUENCE: 48
agcctccggt tctactgcaa                                              20

<210> SEQ ID NO 49
<211> LENGTH: 20
<212> TYPE: DNA
<213> ORGANISM: Turkey Astrovirus

<400> SEQUENCE: 49
ttgcagtaga accggaggct                                              20

<210> SEQ ID NO 50
<211> LENGTH: 328
<212> TYPE: PRT
<213> ORGANISM: Turkey Astrovirus

<400> SEQUENCE: 50

Ser Thr Pro Ala Tyr Pro Lys Phe Gln Ala Tyr Asp Ser Glu Ala Glu
 1               5                  10                  15

Tyr Leu Glu Asp Cys Gly Trp Gln Glu Tyr Leu Asp Val Val Ser Asp
            20                  25                  30

-continued

```
Pro Glu Thr Ile Asn Arg Arg Pro Leu Trp Trp Cys Phe Leu Lys Asn
            35                  40                  45

Glu Val Leu Lys Arg Glu Lys Ile Glu Asp Ser Asp Ile Arg Met Ile
        50                  55                  60

Leu Cys Thr Asp Pro Ile Phe Thr Arg Ile Gly Ala Met Phe Glu Gln
 65                 70                  75                  80

Asp Gln Asn Asn Arg Met Lys Gln Gln Thr Glu Ile Arg Ser Ala Gln
                85                  90                  95

Val Gly Trp Thr Pro Phe Phe Gly Gly Leu Asp Arg Arg Val Arg Arg
            100                 105                 110

Leu Tyr Gly Asp Gly Asp Arg Tyr Phe Val Glu Met Asp Trp Thr Arg
        115                 120                 125

Tyr Asp Gly Thr Ile Pro Lys Ser Leu Phe Trp Arg Ile Arg Gln Ile
130                 135                 140

Arg Phe Phe Phe Leu His Asp Ser His Lys Thr Pro Lys Met Arg Arg
145                 150                 155                 160

Leu Tyr Asn Trp Tyr Val Lys Asn Leu Leu Glu Lys Ile Ile Leu Leu
                165                 170                 175

Pro Thr Gly Glu Val Cys Gln Val Lys Lys Gly Asn Pro Ser Gly Gln
            180                 185                 190

Phe Ser Thr Thr Val Asp Asn Asn Met Ile Asn Val Trp Leu Thr Thr
        195                 200                 205

Phe Glu Val Ser Tyr Leu Phe Phe Lys Gln Arg Gly Arg Leu Pro Thr
210                 215                 220

Glu Lys Glu Leu Gln Glu Asn Cys Ser Met Ile Cys Tyr Gly Asp Asp
225                 230                 235                 240

Arg Leu Leu Ser Ile Arg Lys Gly Phe Val Glu Tyr Glu Pro Asp Thr
                245                 250                 255

Val Ile Asp Met Tyr Lys Asn Ile Phe Gly Met Trp Val Lys Arg Asn
            260                 265                 270

Asn Ile Lys Ile Gln Asp Thr Pro Glu Gly Leu Ser Phe Cys Gly Leu
        275                 280                 285

Thr Ile Val Lys Ser Ser Thr Gly Ala Tyr Val Gly Val Pro Asn Val
290                 295                 300

Asn Lys Ile Leu Ser Thr Leu Glu Asn Pro Val Arg Arg Leu Pro Asp
305                 310                 315                 320

Val Glu Ser Leu Trp Gly Lys Leu
                325

<210> SEQ ID NO 51
<211> LENGTH: 317
<212> TYPE: PRT
<213> ORGANISM: Human astrovirus type 3

<400> SEQUENCE: 51

Ser Thr Pro Ala Tyr Pro Lys Met Asn Tyr Phe Asp Thr Glu Glu Glu
 1               5                  10                  15

Tyr Leu Glu Ala His Gly Trp Ala Pro Tyr Ile Arg Glu Phe Thr Arg
            20                  25                  30

Val Phe Lys Gly Glu Lys Pro Glu Val Leu Trp Tyr Leu Phe Leu Lys
        35                  40                  45

Lys Glu Ile Ile Lys Glu Glu Lys Ile Lys Asn Ser Asp Ile Arg Gln
    50                  55                  60

Ile Val Cys Ala Asp Pro Ile Tyr Thr Arg Ile Gly Ala Cys Leu Glu
 65                 70                  75                  80
```

```
Ala His Gln Asn Ala Leu Met Lys Gln His Thr Gly Thr Ser Val Gly
                85                  90                  95

Arg Cys Gly Trp Ser Pro Met Glu Gly Gly Phe Lys Lys Thr Met Gln
            100                 105                 110

Arg Leu Val Asn Arg Gly Asn Arg Tyr Phe Ile Glu Phe Asp Trp Thr
        115                 120                 125

Arg Tyr Asp Gly Thr Ile Pro Pro Ala Leu Phe Arg His Ile Lys Glu
    130                 135                 140

Ile Arg Trp Asn Phe Ile Asn Lys Asp Gln Arg Glu Lys Tyr Arg His
145                 150                 155                 160

Val His Glu Trp Tyr Val Asp Asn Leu Leu Asn Arg His Val Leu Leu
                165                 170                 175

Pro Ser Gly Glu Val Thr Val Gln Thr Arg Gly Asn Pro Ser Gly Gln
            180                 185                 190

Phe Ser Thr Thr Met Asp Asn Asn Met Val Asn Phe Trp Leu Gln Ala
        195                 200                 205

Phe Glu Phe Ala Tyr Phe Asn Gly Pro Asn Lys Glu Leu Trp Lys Thr
    210                 215                 220

Tyr Asp Thr Val Val Tyr Gly Asp Asp Arg Leu Ser Thr Thr Pro Ser
225                 230                 235                 240

Val Pro Asp Asn Tyr Glu Arg Val Ile Ala Met Tyr Arg Asp Ile
                245                 250                 255

Phe Gly Met Trp Val Lys Pro Gly Lys Val Ile Cys Arg Glu Ser Ile
            260                 265                 270

Ile Gly Leu Ser Phe Cys Gly Phe Thr Val Asn Ser Asp Leu Glu Pro
        275                 280                 285

Val Pro Thr Ser Pro Glu Lys Leu Met Ala Ser Leu Leu Lys Pro Tyr
    290                 295                 300

Lys Val Leu Pro Asp Leu Glu Ser Leu His Gly Lys Leu
305                 310                 315

<210> SEQ ID NO 52
<211> LENGTH: 317
<212> TYPE: PRT
<213> ORGANISM: Human astrovirus type 1

<400> SEQUENCE: 52

Ser Thr Pro Ala Tyr Pro Lys Met Asn Tyr Phe Asp Thr Glu Glu Asn
 1               5                  10                  15

Tyr Leu Glu Ala His Gly Trp Ala Pro Tyr Ile Arg Glu Phe Thr Arg
                20                  25                  30

Val Phe Lys Gly Asp Lys Pro Glu Val Leu Trp Tyr Leu Phe Leu Lys
            35                  40                  45

Lys Glu Ile Ile Lys Glu Glu Lys Ile Arg Asn Ser Asp Ile Arg Gln
        50                  55                  60

Ile Val Cys Ala Asp Pro Ile Tyr Thr Arg Ile Gly Ala Cys Leu Glu
65                  70                  75                  80

Ala His Gln Asn Ala Leu Met Lys Gln His Thr Asp Thr Ser Val Gly
                85                  90                  95

Gln Cys Gly Trp Ser Pro Met Glu Gly Gly Phe Lys Lys Thr Met Gln
            100                 105                 110

Arg Leu Val Asn Lys Gly Asn Lys His Phe Ile Glu Phe Asp Trp Thr
        115                 120                 125

Arg Tyr Asp Gly Thr Ile Pro Pro Ala Leu Phe Lys His Ile Lys Glu
```

```
            130                 135                 140
Ile Arg Trp Asn Phe Ile Asn Lys Asp Gln Arg Glu Lys Tyr Arg His
145                 150                 155                 160
Val His Glu Trp Tyr Val Asp Asn Leu Leu Asn Arg His Val Leu Leu
                165                 170                 175
Pro Ser Gly Glu Val Thr Leu Gln Thr Arg Gly Asn Pro Ser Gly Gln
            180                 185                 190
Phe Ser Thr Thr Met Asp Asn Asn Met Val Asn Phe Trp Leu Gln Ala
        195                 200                 205
Phe Glu Phe Ala Tyr Phe Asn Gly Pro Asp Arg Asp Leu Trp Lys Thr
    210                 215                 220
Tyr Asp Thr Val Val Tyr Gly Asp Asp Arg Leu Ser Thr Thr Pro Ser
225                 230                 235                 240
Val Pro Asp Asp Tyr Glu Glu Arg Val Ile Thr Met Tyr Arg Asp Ile
                245                 250                 255
Phe Gly Met Trp Val Lys Pro Gly Lys Val Ile Cys Arg Asp Ser Ile
            260                 265                 270
Val Gly Leu Ser Phe Cys Gly Phe Thr Val Asn Glu Asn Leu Glu Pro
        275                 280                 285
Val Pro Thr Ser Pro Glu Lys Leu Met Ala Ser Leu Leu Lys Pro Tyr
    290                 295                 300
Lys Ile Leu Pro Asp Leu Glu Ser Leu His Gly Lys Leu
305                 310                 315

<210> SEQ ID NO 53
<211> LENGTH: 310
<212> TYPE: PRT
<213> ORGANISM: Human astrovirus type 2

<400> SEQUENCE: 53

Met Asn Tyr Phe Asp Thr Glu Glu Ser Tyr Leu Glu Ala His Gly Trp
1               5                   10                  15
Ala Pro Tyr Ile Arg Glu Phe Thr Arg Val Phe Lys Gly Asp Lys Pro
            20                  25                  30
Glu Val Leu Trp Tyr Leu Phe Leu Lys Lys Glu Ile Ile Lys Glu Glu
        35                  40                  45
Lys Val Lys Asn Ser Asp Ile Arg Gln Ile Val Cys Ala Asp Pro Ile
    50                  55                  60
Tyr Thr Arg Ile Gly Ala Cys Leu Glu Ala His Gln Asn Ala Leu Met
65                  70                  75                  80
Lys Gln His Thr Asp Thr Ser Val Gly Gln Cys Gly Trp Ser Pro Met
                85                  90                  95
Glu Gly Gly Phe Lys Lys Thr Met Gln Arg Leu Val Asn Lys Gly Asn
            100                 105                 110
Lys Tyr Phe Ile Glu Phe Asp Trp Thr Arg Tyr Asp Gly Thr Ile Pro
        115                 120                 125
Pro Ala Leu Phe Lys His Ile Lys Glu Ile Arg Trp Asn Phe Ile Asn
    130                 135                 140
Lys Asp Gln Arg Glu Lys Tyr Arg His Val His Asp Trp Tyr Val Asp
145                 150                 155                 160
Asn Leu Leu Asn Arg His Val Leu Leu Pro Ser Gly Glu Val Thr Leu
                165                 170                 175
Gln Thr Arg Gly Asn Pro Ser Gly Gln Phe Ser Thr Thr Met Asp Asn
            180                 185                 190
```

-continued

```
Asn Met Val Asn Phe Trp Leu Gln Ala Phe Glu Phe Ala Tyr Phe Asn
        195                 200                 205

Gly Pro Asp Lys Asp Leu Trp Lys Thr Tyr Asp Thr Val Val Tyr Gly
    210                 215                 220

Asp Asp Arg Leu Ser Thr Thr Pro Ser Val Pro Asp Asp Tyr Glu Glu
225                 230                 235                 240

Arg Val Ile Thr Met Tyr Arg Asp Ile Phe Gly Met Trp Val Lys Pro
                245                 250                 255

Gly Lys Val Ile Cys Arg Asn Ser Ile Val Gly Leu Ser Phe Cys Gly
            260                 265                 270

Phe Thr Val Asn Glu Asn Leu Glu Pro Val Pro Thr Ser Pro Glu Lys
        275                 280                 285

Leu Met Ala Ser Leu Leu Lys Pro Tyr Lys Val Leu Pro Asp Leu Glu
    290                 295                 300

Ser Leu His Gly Lys Leu
305                 310

<210> SEQ ID NO 54
<211> LENGTH: 119
<212> TYPE: PRT
<213> ORGANISM: Human poliovirus 1

<400> SEQUENCE: 54

Val Ala Ile Leu Pro Thr His Ala Ser Pro Gly Glu Ser Ile Val Ile
  1               5                  10                  15

Asp Gly Lys Glu Val Glu Ile Leu Asp Ala Lys Ala Leu Glu Asp Gln
             20                  25                  30

Ala Gly Thr Asn Leu Glu Ile Thr Ile Ile Thr Leu Lys Arg Asn Glu
         35                  40                  45

Lys Phe Arg Asp Ile Arg Pro His Ile Pro Thr Gln Ile Thr Glu Thr
     50                  55                  60

Asn Asp Gly Val Leu Ile Val Asn Thr Ser Lys Tyr Pro Asn Met Tyr
 65                  70                  75                  80

Val Pro Val Gly Ala Val Thr Glu Gln Gly Tyr Leu Asn Leu Gly Gly
                 85                  90                  95

Arg Gln Arg Ala Gly Gln Cys Gly Gly Val Ile Thr Cys Thr Gly Lys
            100                 105                 110

Val Ile Gly Met His Val Gly
        115

<210> SEQ ID NO 55
<211> LENGTH: 126
<212> TYPE: PRT
<213> ORGANISM: Human astrovirus type 3

<400> SEQUENCE: 55

Asp Ile Val Thr Ala Ala His Val Val Gly Asn Asn Thr Phe Val Asn
  1               5                  10                  15

Val Cys Tyr Glu Gly Leu Met Tyr Glu Ala Lys Val Arg Tyr Met Pro
             20                  25                  30

Glu Lys Asp Ile Ala Phe Ile Thr Cys Pro Gly Asp Leu His Pro Thr
         35                  40                  45

Ala Arg Leu Lys Leu Ser Lys Asn Pro Asp Tyr Ser Cys Val Thr Val
     50                  55                  60

Met Ala Tyr Val Asn Glu Asp Leu Val Val Ser Thr Ala Ala Ala Met
 65                  70                  75                  80
```

```
Val His Gly Asn Thr Leu Ser Tyr Ala Val Arg Thr Gln Asp Gly Met
                85                  90                  95

Ser Gly Ala Pro Val Cys Asp Lys Tyr Gly Arg Val Leu Ala Val His
            100                 105                 110

Gln Thr Asn Thr Gly Tyr Thr Gly Gly Ala Val Ile Ile Asp
        115                 120                 125
```

<210> SEQ ID NO 56
<211> LENGTH: 126
<212> TYPE: PRT
<213> ORGANISM: Human astrovirus type 1

<400> SEQUENCE: 56

```
Asp Ile Val Thr Ala Ala His Val Val Gly Asn Asn Thr Phe Val Asn
 1               5                  10                  15

Val Cys Tyr Glu Gly Leu Met Tyr Glu Ala Lys Val Arg Tyr Met Pro
            20                  25                  30

Glu Lys Asp Ile Ala Phe Val Thr Cys Pro Gly Asp Leu His Pro Thr
        35                  40                  45

Ala Arg Leu Lys Leu Ser Lys Asn Pro Asp Tyr Ser Cys Val Thr Val
    50                  55                  60

Met Ala Tyr Val Asn Glu Asp Leu Val Val Ser Thr Ala Ala Ala Met
65                  70                  75                  80

Val His Gly Asn Thr Leu Ser Tyr Ala Val Arg Thr Gln Asp Gly Met
                85                  90                  95

Ser Gly Ala Pro Val Cys Asp Lys Tyr Gly Arg Val Leu Ala Val His
            100                 105                 110

Gln Thr Asn Thr Gly Tyr Thr Gly Gly Ala Val Ile Ile Asp
        115                 120                 125
```

<210> SEQ ID NO 57
<211> LENGTH: 126
<212> TYPE: PRT
<213> ORGANISM: Human astrovirus type 2

<400> SEQUENCE: 57

```
Asp Ile Val Thr Ala Ala His Val Val Gly Asn Asn Thr Phe Val Asn
 1               5                  10                  15

Val Cys Tyr Glu Gly Leu Met Tyr Glu Ala Lys Val Arg Tyr Met Pro
            20                  25                  30

Glu Lys Asp Ile Ala Phe Ile Thr Cys Pro Gly Asp Leu His Pro Thr
        35                  40                  45

Ala Arg Leu Lys Leu Ser Lys Asn Pro Asp Tyr Ser Tyr Val Thr Val
    50                  55                  60

Met Ala Tyr Val Asn Glu Asp Leu Val Val Ser Thr Ala Ala Ala Met
65                  70                  75                  80

Val His Gly Asn Thr Leu Ser Tyr Ala Val Arg Thr Gln Asp Gly Met
                85                  90                  95

Ser Gly Ala Pro Val Cys Asp Lys Tyr Gly Arg Val Leu Ala Val His
            100                 105                 110

Gln Thr Asn Thr Gly Tyr Thr Gly Gly Ala Val Ile Ile Asp
        115                 120                 125
```

<210> SEQ ID NO 58
<211> LENGTH: 133
<212> TYPE: PRT
<213> ORGANISM: Turkey Astrovirus -continued

```
<400> SEQUENCE: 58

Tyr Ile Leu Thr Ala Glu His Val Val Gln Gly Ser Asp Ile Ala Thr
  1               5                  10                  15

Leu Lys Asn Gly Ser Val Ser Val Lys Ser Lys Val Ile Lys Thr Ile
             20                  25                  30

Pro Ile Phe Glu Ser Val Asp Asn Val Ala Val Leu Lys Leu Pro Pro
         35                  40                  45

Glu Leu Asn Ser Val Lys Pro Ile Lys Leu Ala Lys Lys Val Gln Ser
     50                  55                  60

Asp Tyr Leu Thr Leu Thr Ala Tyr Asp Pro Asn Phe Gln His Ala Val
 65                  70                  75                  80

Thr Phe Thr Gly Trp Cys Ile Ile Asp Gly Asn Trp Leu Asn Asn Ser
                 85                  90                  95

Phe Asp Thr Lys Phe Gly Asn Ser Gly Ala Pro Tyr Cys Asp His Asp
            100                 105                 110

Gly Arg Leu Val Gly Ile His Leu Gly Thr Gln Gly Val Leu Gln Gly
        115                 120                 125

Ile Val Ile Val Asp
        130

<210> SEQ ID NO 59
<211> LENGTH: 78
<212> TYPE: RNA
<213> ORGANISM: Turkey Astrovirus

<400> SEQUENCE: 59
gucaaaaaaa cuaauagagg ggccugugac aacaaaggcc ccuacccccg uaccagauug      60
gcuuaaaaua uuugcaug                                                   78

<210> SEQ ID NO 60
<211> LENGTH: 1125
<212> TYPE: PRT
<213> ORGANISM: Turkey Astrovirus

<400> SEQUENCE: 60

Met Ala Gln Ala Gly Arg Ser Gly Asp Ala Phe Ala Ser Leu Asp Gln
  1               5                  10                  15

Arg Arg Glu Arg Gln Glu Glu Gln Ala Gln Ser Gly Leu Asp Lys Val
             20                  25                  30

Phe Tyr Phe Gln Gly Val Val Glu Leu Phe Asn Arg Met Lys Ile Ala
         35                  40                  45

Tyr Gly Arg Thr Pro Ala Trp Thr Ala Leu Met Lys Cys Asn Ala Ile
     50                  55                  60

Tyr Leu Lys Asp Phe Lys Thr Ala Val Gly Val Glu Gly Thr Arg Tyr
 65                  70                  75                  80

Gly Leu Phe Phe Ala Glu Glu Val Thr Lys Pro Thr Trp Ser Pro Asp
                 85                  90                  95

Ile Gly Ala Asn Leu Ile Thr Leu Gly Glu Lys Ala Cys Leu Asp Ala
            100                 105                 110

Gln Asn Ala Lys Tyr Glu Arg Leu Gln Ala Ser Leu Lys Thr Thr Ser
        115                 120                 125

Gly Leu Val His Gln Val Met Glu Lys Thr Arg Glu Ala Lys Glu Asn
    130                 135                 140

Leu Glu Lys Ala Asn Lys Ile Gln Glu Gln Leu Asp Lys Val Ile Glu
145                 150                 155                 160
```

-continued

```
Ser Asn Lys Ala Leu His Arg Lys Ile Gln Glu Arg Asn Arg Glu Lys
                165                 170                 175

Met Gln Glu Tyr Met Val Arg Leu His Asn Thr Gln Lys Asp Arg Asp
            180                 185                 190

Asp Trp Val Gln Arg Cys Ser Arg Leu Glu Gln Glu Asn Val Thr Leu
        195                 200                 205

Gln Lys Arg Leu Lys Glu Lys Glu Asn Ala Leu Val Ser Val Gly Trp
    210                 215                 220

Asp Leu Leu Gly Trp Ile Val Ile Ser Val Leu Val Phe Gly Leu Ile
225                 230                 235                 240

Ser Leu Ala Asp Ala Gln Asn Leu Thr Pro Pro Ala Lys Ile Val Ile
                245                 250                 255

Thr Pro Gly Gln Ala Glu Phe Met Asp Leu Ala Lys Leu Glu Lys Ile
            260                 265                 270

Gln Val Arg Lys Tyr Arg Leu Asp Ser Cys Glu Leu Pro Pro Glu Lys
        275                 280                 285

Gly Cys Val Leu Tyr Lys Asp Tyr Leu Thr Thr Arg Pro Val Ser Phe
    290                 295                 300

Leu Glu Leu Met Ala Lys Cys Ser Lys Pro Asp Trp Val Ser Glu Ser
305                 310                 315                 320

Ser Tyr Asn Glu Thr Thr Leu Met Glu Glu Cys Ile Gln Ile Phe Gly
                325                 330                 335

Ala Glu Trp Cys Glu Gly Lys Leu Val Asp Leu Val Pro Arg Lys Cys
            340                 345                 350

Gly Glu Gln His Val Leu Val Asn Ile Ile Glu Gln Ile Glu Lys Thr
        355                 360                 365

Arg Glu Val Val Thr Leu Ile Tyr Gly Lys Val Met Ser Tyr Arg Leu
    370                 375                 380

Asp Met Trp Ile Thr Ser Ile Phe Ser Leu Val Leu Ala Gly Asn Lys
385                 390                 395                 400

Glu Lys Leu Phe Lys Met Ala Pro Phe Ile Phe Val Ala Trp Phe Leu
                405                 410                 415

Asn Ile Pro Val Phe Leu Thr Cys Val Ala Val Asn Ile Phe Pro Val
            420                 425                 430

Val Ser Leu Pro Phe Ile Leu Phe Gln Ile Phe Met Pro Gln Phe Val
        435                 440                 445

Leu Val Asn Ala Phe Leu Leu Trp Leu Thr Leu Thr Leu Thr Ala Phe
    450                 455                 460

Tyr Trp Ser Glu Gly Pro Lys Ile Leu Met Glu Ile Ser Tyr Ala Leu
465                 470                 475                 480

Val Tyr Thr Ile Gly Phe Val Leu Trp Ser Leu Gly Leu Ala Val Gly
                485                 490                 495

Val Thr Leu Lys Leu Thr Met Val His Gln Ile Leu Met Phe Cys Val
            500                 505                 510

Val Ala Ala Ile Cys Gly Thr Lys Phe Ala Cys Thr Thr Ile Thr
        515                 520                 525

Val Gln His Pro Asp Gly Thr Thr Ala Lys Tyr Thr Arg Val Gly Lys
    530                 535                 540

Leu Lys Asn Asn Val Val Asn Gln Cys Lys Val Val Thr Thr Leu
545                 550                 555                 560

Gln Thr Arg Gly Val Ile Pro Ala Thr Pro Ala Lys Thr Ala Ser Ile
                565                 570                 575

Val Ile Val Glu Gly Lys Asn Gly Thr Gly Val Gly Phe Arg Phe Met
```

-continued

```
                580                 585                 590
Asn Tyr Ile Leu Thr Ala Glu His Val Val Gln Gly Ser Asp Ile Ala
            595                 600                 605
Thr Leu Lys Asn Gly Ser Val Ser Val Lys Ser Lys Val Ile Lys Thr
610                 615                 620
Ile Pro Ile Phe Glu Ser Val Asp Asn Val Ala Val Leu Lys Leu Pro
625                 630                 635                 640
Pro Glu Leu Asn Ser Val Lys Pro Ile Lys Leu Ala Lys Lys Val Gln
            645                 650                 655
Ser Asp Tyr Leu Thr Leu Thr Ala Tyr Asp Pro Asn Phe Gln His Ala
            660                 665                 670
Ala Thr Phe Thr Gly Trp Cys Ile Ile Asp Gly Asn Trp Leu Asn Asn
            675                 680                 685
Ser Phe Asp Thr Lys Phe Gly Asn Ser Gly Ala Pro Tyr Cys Asp His
            690                 695                 700
Asp Gly Arg Leu Val Gly Ile His Leu Gly Thr Gln Gly Val Leu Ser
705                 710                 715                 720
Gln Gly Ile Val Ile Val Asp Ala Leu Lys Asn Thr Phe Gln Leu Ala
            725                 730                 735
Asp Gln Cys Arg Pro Gln Asn Phe Asp Met Asp Glu Phe Leu Glu Lys
            740                 745                 750
Val Ile Ala Gly Thr Lys Val Ser His Ala Ala Ile Leu Lys Glu Leu
            755                 760                 765
Glu Glu Leu Arg Glu Glu Val Gln Phe Leu Lys Lys Lys Cys Val Thr
770                 775                 780
Tyr Asp Asp Tyr Trp Leu Cys Gln Thr Ile Phe Gly Gln Ala Lys Gly
785                 790                 795                 800
Lys Thr Lys Lys Thr Val Arg Gly Arg Lys His Leu Val Thr Lys Arg
            805                 810                 815
Ala Leu Gly Lys Gly His Phe Met Lys Met Arg Met Leu Thr Asp Glu
            820                 825                 830
Glu Tyr Gln Asn Met Ile Glu Lys Gly Phe Ser Ala Glu Glu Ile Arg
            835                 840                 845
Glu Ala Val Asn Ala Leu Arg Glu Gln Ala Trp Leu Asn Tyr Cys Ile
            850                 855                 860
Asp Asn Asp Val Asp Asp Glu Gly Glu Glu Asp Asp Trp Tyr Asp Asp
865                 870                 875                 880
Met Val Glu Thr Asp Arg Val Asn Gln Glu Ile Asp Glu Ala Ile Glu
                        885                 890                 895
Arg Ala Met Glu Asp Arg Gly Glu Phe Tyr Gln Lys Lys Ser Arg Leu
            900                 905                 910
Thr Phe Val Glu Gln Ala Met Met His Leu Ile Gln Val Ser Lys Glu
            915                 920                 925
Arg Ser Gln Thr Ala Lys Leu Glu Val Gln Lys Glu Asn Glu Ala Gln
            930                 935                 940
Leu Val Lys Met Phe Glu Arg Cys Val Thr Asp Glu Asn Thr Pro Glu
945                 950                 955                 960
Gly Thr Thr Ser Ile Ala Ala Leu Ser Thr Glu Asp Asp Val Arg Leu
                        965                 970                 975
Val Glu Gly Lys Val Ile Asp Phe Thr Lys Ala Lys Asn Ile Pro Val
            980                 985                 990
Asp Gly Glu Ile Arg Arg Glu Ile Ile Pro Gly Thr Lys Cys Thr Glu
            995                 1000                1005
```

```
Ile Ser Thr Gly Pro Glu Asn Lys Lys Asn Ile Leu Lys Lys Lys Asp
    1010                1015                1020

Thr His Ile Ala Glu Gly Lys Val Glu Thr Lys Ser Ser Gln Gln Pro
1025                1030                1035                1040

Val Asp Val Lys Asp Asp Lys Pro Val Ala Leu Glu Gln Arg Lys Pro
                1045                1050                1055

Arg Ala Cys Lys Trp Cys Gly Ser Ser Gln Lys His Asp Tyr Arg Glu
            1060                1065                1070

Cys Arg Phe Gln Arg Glu Lys Arg Phe Cys Val Tyr Cys Ala Ala Met
        1075                1080                1085

His Ser Met Phe Glu Gly His Ile Arg Pro Ile Glu Cys Thr Ser Cys
    1090                1095                1100

Lys Lys Ser Phe Ser Gly Ile Glu Lys Leu Glu Asp His Val Val Ser
1105                1110                1115                1120

Gly Glu Cys Lys Asn
            1125

<210> SEQ ID NO 61
<211> LENGTH: 527
<212> TYPE: PRT
<213> ORGANISM: Turkey Astrovirus

<400> SEQUENCE: 61

Glu Val Arg Arg Ser Cys Gly Gln Trp Arg Val Ser Lys Lys Leu Ile
1               5                   10                  15

Glu Gly Pro Val Thr Thr Lys Ala Pro Thr Pro Val Pro Asp Trp Leu
                20                  25                  30

Lys Ile Phe Ala Trp Glu Asp Asp Ile Leu Pro Pro Glu Gly Lys Thr
            35                  40                  45

Ala Leu Pro Glu Asn Val Thr Leu Ile Gly His Ile Pro Val Asp Lys
        50                  55                  60

Leu Val Ser Arg Thr Lys Lys Val Gln Asp Pro Leu Leu Gly Leu Val
65                  70                  75                  80

Thr Pro Trp Lys Gln Asp Met Tyr Asp Ser Thr Thr Trp Thr Val Lys
                85                  90                  95

Ala Tyr Thr Lys Met Phe Glu Lys Phe His Tyr His Asp Pro Val Asp
            100                 105                 110

Phe Val Glu Gln Tyr Ala Glu Phe Val Leu Leu Cys Asp Asn Met Val
        115                 120                 125

Leu Arg Glu His Asp Tyr Met Ala Asn Ser Asn Ile Thr Pro Ile Met
130                 135                 140

Ser Thr Glu Lys Asn Val Asn Ser Thr Pro Ala Tyr Pro Lys Phe Gln
145                 150                 155                 160

Ala Tyr Asp Ser Glu Ala Glu Tyr Leu Glu Asp Cys Gly Trp Gln Glu
                165                 170                 175

Tyr Leu Asp Val Val Ser Asp Pro Glu Thr Ile Asn Arg Arg Pro Leu
            180                 185                 190

Trp Trp Cys Phe Leu Lys Asn Glu Val Leu Lys Arg Glu Lys Ile Glu
        195                 200                 205

Asp Ser Asp Ile Arg Met Ile Leu Cys Thr Asp Pro Ile Phe Thr Arg
    210                 215                 220

Ile Gly Ala Met Phe Glu Gln Asp Gln Asn Asn Arg Met Lys Gln Gln
225                 230                 235                 240

Thr Glu Ile Arg Ser Ala Gln Val Gly Trp Thr Pro Phe Phe Gly Gly
```

```
                     245                 250                 255
Leu Asp Arg Arg Val Arg Arg Leu Tyr Gly Asp Gly Asp Arg Tyr Phe
                260                 265                 270
Val Glu Met Asp Trp Thr Arg Tyr Asp Gly Thr Ile Pro Lys Ser Leu
            275                 280                 285
Phe Trp Arg Ile Arg Gln Ile Arg Phe Phe Leu His Asp Ser His
        290                 295                 300
Lys Thr Pro Lys Met Arg Arg Leu Tyr Asn Trp Tyr Val Lys Asn Leu
305                 310                 315                 320
Leu Glu Lys Ile Ile Leu Leu Pro Thr Gly Glu Val Cys Gln Val Lys
                325                 330                 335
Lys Gly Asn Pro Ser Gly Gln Phe Ser Thr Thr Val Asp Asn Asn Met
                340                 345                 350
Ile Asn Val Trp Leu Thr Thr Phe Glu Val Ser Tyr Leu Phe Phe Lys
                355                 360                 365
Gln Arg Gly Arg Leu Pro Thr Glu Lys Glu Leu Gln Glu Asn Cys Ser
            370                 375                 380
Met Ile Cys Tyr Gly Asp Asp Arg Leu Leu Ser Ile Arg Lys Gly Phe
385                 390                 395                 400
Val Glu Tyr Glu Pro Asp Thr Val Ile Asp Met Tyr Lys Asn Ile Phe
                405                 410                 415
Gly Met Trp Val Lys Arg Asn Asn Ile Lys Ile Gln Asp Thr Pro Glu
                420                 425                 430
Gly Leu Ser Phe Cys Gly Leu Thr Ile Val Lys Ser Thr Gly Ala
            435                 440                 445
Tyr Val Gly Val Pro Asn Val Asn Lys Ile Leu Ser Thr Leu Glu Asn
                450                 455                 460
Pro Val Arg Arg Leu Pro Asp Val Glu Ser Leu Trp Gly Lys Leu Val
465                 470                 475                 480
Ser Leu Arg Ile Leu Cys Glu Asn Ala Pro Ser Asn Val Lys His Phe
                485                 490                 495
Leu Asp Glu Gln Ile Ser Asn Val Glu Glu Phe Ala Ala Arg Glu Asn
                500                 505                 510
Ile Gln Leu Pro Glu Val Gly Pro Asp Phe Tyr Ser Arg Ile Trp
            515                 520                 525

<210> SEQ ID NO 62
<211> LENGTH: 724
<212> TYPE: PRT
<213> ORGANISM: Turkey astrovirus

<400> SEQUENCE: 62

Met Ala Ala Met Ala Asp Lys Val Val Lys Lys Thr Thr Thr Arg
 1               5                  10                  15
Arg Arg Gly Arg Ser Asn Ser Arg Ser Arg Ser Arg Ser Arg
                20                  25                  30
Ser Arg Thr Lys Lys Thr Val Lys Ile Glu Lys Lys Pro Glu Lys
            35                  40                  45
Ser Ile Leu Lys Lys Ile Asp Gln Ala Glu Arg Arg Asp Ala Lys Gln
    50                  55                  60
Leu Arg Arg Ile Arg Lys Lys Val Gln Gly Pro Val Asn Ser Arg
65                  70                  75                  80
Met Thr Thr Val Val Thr Leu Gly Gln Ile Thr Gly Asn Lys Asp Asn
                85                  90                  95
```

```
Thr Leu Glu Arg Lys His Lys Cys Phe Leu Asn Pro Leu Leu Met Lys
            100                 105                 110

Ser Gln Glu Thr Gly Gln Thr Ala Thr Pro Leu Ser Val Arg Ala Ser
        115                 120                 125

Gln Tyr Asn Leu Trp Lys Leu Ser Arg Leu His Val Arg Leu Ile Pro
    130                 135                 140

Leu Ala Gly Lys Ala Asn Ile Leu Gly Ser Val Val Phe Leu Asp Leu
145                 150                 155                 160

Glu Gln Glu Ala Asn Thr Ala Gly Pro Glu Ser Val Asp Thr Ile Lys
                165                 170                 175

Ala Arg Pro His Val Glu Val Pro Ile Gly Ser Lys Thr Val Trp Lys
            180                 185                 190

Val His Pro Arg Ser Ala Leu Gly Pro Arg Gln Gly Trp Trp Asn Val
        195                 200                 205

Asp Pro Gly Asp Ser Pro Thr Asp Ser Leu Gly Pro Ala Leu Asn Met
    210                 215                 220

Trp Thr Tyr Leu Gln Thr Val Asn Ala Leu Gln Ser Ala Gly Gly Thr
225                 230                 235                 240

Gln Thr Pro Tyr Thr Ser Ala Leu Phe Leu Val Glu Val Leu Val Thr
                245                 250                 255

Tyr Glu Phe Ser Asn Tyr Gly Pro Lys Pro Ala Leu Ser Gln Met Val
            260                 265                 270

Ser Asp Ser Phe Pro Pro Ala Ser Gly Ser Thr Ala Thr Leu Lys Asn
        275                 280                 285

Thr Ser Asp Gly Ala Val Ala Ile Gln Leu Ser Gly Ala Ile Ala Arg
    290                 295                 300

Lys Met Glu Glu Val Glu Pro Lys Gly Arg Arg Ser Asn Ala Gln Thr
305                 310                 315                 320

Ser Gly Val Gly Glu Val Phe Trp Ala Val Ser Thr Glu Val Val Asn
                325                 330                 335

Thr Val Ala Asp Ala Ile Pro Gly Trp Gly Trp Leu Leu Lys Gly Gly
            340                 345                 350

Trp Phe Val Leu Arg Lys Ile Phe Gly Ala Ala Asn Asp Gln Asn Gly
        355                 360                 365

Thr Tyr Leu Ile Tyr Ser Val Ala Asp Ala Gln Gly Asp Asn Arg
    370                 375                 380

Ile Tyr Thr Ser Val Lys Gln Thr Gln Leu Thr Ser Ser Arg Ile Asn
385                 390                 395                 400

Leu Val Gln Leu Thr Gln Pro Asn Val Asn Gln Ala Val Gly Gly
                405                 410                 415

Ser Val Gly Ala Ala Asn Ser Ile Tyr Leu Pro Leu Pro Gln Ala Asp
            420                 425                 430

Asp Gln Tyr Thr Pro Tyr Phe Val Tyr Asn Phe Gln Gly Glu Arg Val
        435                 440                 445

Ser Thr Thr Glu Thr Gly Val Phe Cys Leu Ala Ala Ile Pro Ala Ala
    450                 455                 460

Thr Thr Ser Ser Arg Tyr Asn Asn Gln Ile Thr Thr Pro Ser Ile Gly
465                 470                 475                 480

Tyr Arg Asn Ala Ser Gly Thr Gly Thr Ser Phe Leu Leu Asp Ala Ala
                485                 490                 495

Ser Trp Trp Asn Ile Leu Asp Val Thr Gln Thr Gly Val Leu Phe Gly
            500                 505                 510

Gln Pro Arg Leu Gly Val Gly Val Met Gln Thr Met Lys Thr Leu Lys
```

```
                515                 520                 525
Gln His Ile Lys Asp Tyr Thr Glu Pro Ala Ile Gln Lys Tyr Tyr Pro
    530                 535                 540
Gly Thr Thr Asn Leu Asp Glu Gln Leu Lys Gln Arg Leu Asn Leu Ala
545                 550                 555                 560
Glu Gly Asp Pro Val Ile Ser Met Gly Asp Thr Asn Gly Arg Arg Ala
                565                 570                 575
Ala Leu Phe Tyr Arg Thr Ser Asp Glu Lys Tyr Ile Leu Phe Phe Ser
            580                 585                 590
Thr Thr Glu Asp Pro Gly Ala Gln Tyr Gln Asn Leu Lys Met Leu Tyr
            595                 600                 605
Phe Trp Asn Trp Ser Tyr Ser Asp Thr Lys Gln Phe Leu Asp His
        610                 615                 620
Leu Arg Thr Val Gln Phe Ala Asn Leu Asp Asp Ser Gln Pro Ala Pro
625                 630                 635                 640
Tyr Asp Ser Asp Asp Asp Leu Ser Asp Val Thr Ser Leu Phe Glu
                645                 650                 655
Gln Ala Asp Leu Gly Asp Glu Thr Asp Phe Lys Phe Asn Met Ser Ile
            660                 665                 670
Gln Thr Ser Lys His Leu Glu Glu Glu Lys Asn Tyr Trp Lys Asn Gln
            675                 680                 685
Cys Glu Arg Met Met Met Glu Lys Ala Leu Ser Gly Thr Ser Gln Pro
        690                 695                 700
Leu Val Arg Phe Glu Lys Ala Gly Pro Arg Ala Asp Gln Ser Ser Ala
705                 710                 715                 720
Ser Gly His Ser

<210> SEQ ID NO 63
<211> LENGTH: 7
<212> TYPE: RNA
<213> ORGANISM: Turkey Astrovirus

<400> SEQUENCE: 63 aaaaaau                                                                    7

<210> SEQ ID NO 64
<211> LENGTH: 4
<212> TYPE: PRT
<213> ORGANISM: Turkey Astrovirus

<400> SEQUENCE: 64

Tyr Gly Asp Asp
  1

<210> SEQ ID NO 65
<211> LENGTH: 4
<212> TYPE: PRT
<213> ORGANISM: Turkey Astrovirus

<400> SEQUENCE: 65

Arg Asp Arg Pro
  1
```